(12) United States Patent
De Maria et al.

(10) Patent No.: US 9,173,421 B2
(45) Date of Patent: Nov. 3, 2015

(54) THERMOSTABLE PHYTASE VARIANTS

(75) Inventors: Leonardo De Maria, Frederiksberg (DK); Lars Kobberoee Skov, Ballerup (DK); Michael Skjoet, Roskilde (DK)

(73) Assignee: Novozymes A/S, Bagsvaerd (DK)

( * ) Notice: Subject to any disclaimer, the term of this patent is extended or adjusted under 35 U.S.C. 154(b) by 487 days.

(21) Appl. No.: 13/636,008

(22) PCT Filed: Mar. 25, 2011

(86) PCT No.: PCT/EP2011/054640
§ 371 (c)(1),
(2), (4) Date: Sep. 19, 2012

(87) PCT Pub. No.: WO2011/117397
PCT Pub. Date: Sep. 29, 2011

(65) Prior Publication Data
US 2013/0040342 A1    Feb. 14, 2013

Related U.S. Application Data

(60) Provisional application No. 61/318,024, filed on Mar. 26, 2010.

(30) Foreign Application Priority Data

Mar. 26, 2010    (EP) .................................... 10158026

(51) Int. Cl.
| | | |
|---|---|---|
| *C12N 9/16* | (2006.01) | |
| *C12N 15/00* | (2006.01) | |
| *C12P 7/00* | (2006.01) | |
| *A23K 1/18* | (2006.01) | |
| *A23K 1/00* | (2006.01) | |
| *A23K 1/165* | (2006.01) | |
| *C12P 7/06* | (2006.01) | |

(52) U.S. Cl.
CPC ............. *A23K 1/1826* (2013.01); *A23K 1/006* (2013.01); *A23K 1/1656* (2013.01); *C12N 9/16* (2013.01); *C12P 7/06* (2013.01); *C12Y 301/03008* (2013.01); *Y02E 50/17* (2013.01)

(58) Field of Classification Search
CPC .................................. C12N 9/16; C12N 15/00
See application file for complete search history.

(56) References Cited

U.S. PATENT DOCUMENTS

2009/0047387 A1* 2/2009 De Maria et al. ............... 426/63

FOREIGN PATENT DOCUMENTS

| WO | 2006/043178 A2 | 4/2006 |
| WO | 2007/112739 A1 | 10/2007 |
| WO | 2008/036916 A2 | 3/2008 |
| WO | 2008/092901 A2 | 8/2008 |
| WO | 2008/097619 A2 | 8/2008 |
| WO | 2009/100183 A2 | 8/2009 |

OTHER PUBLICATIONS

Takag et al. Enhancement of the thermostability of subtilisin E by introduction of a disulfide bond engineered on the basis of structural comparison with a thermophilic serine protease. J Biol Chem. Apr. 25, 1990;265(12):6874-8.*
Kim et al., Appl. Microbiol. Biotechnol., vol. 79, No. 5, pp. 751-758 (2008).
Lim et al., Nature Structure Biology, vol. 7, No. 2, pp. 108-113 (2000).
Mu et al., New Biotechnology, vol. 25, Suppl. 1, p. S86, abstract No. 2.1.106 (2009).
Mullaney et al., Biochemical and Biophysical Research Communications, vol. 328, No. 2, pp. 404-408 (2005).
Mullaney et al., Appl. Microbiol. Biotechnol., vol. 87, No. 4, pp. 1367-1372 (2010).
Rodriguez et al., Archives of Biochemistry and Biophysics, vol. 382, No. 1, pp. 105-112 (2000).
Zinin et al, UniProt Database, Accession No. Q6U677 (2004).
Zinin et al, FEMS Microbiology Letters, vol. 236, pp. 283-290 (2004).

* cited by examiner

*Primary Examiner* — Yong Pak
(74) *Attorney, Agent, or Firm* — Elias Lambiris

(57) ABSTRACT

The present invention relates to a method for producing phytase variants has at least 70% identity to a phytase derived from *Buttiauxella* and comprises at least one additional disulfide bond as compared to this phytase. These phytase variants have modified, preferably improved, properties, such as thermostability, temperature profile, pH profile, specific activity, performance in animal feed, reduced protease sensitiliby, and/or an modified glycosylation pattern. The invention also relates to the variants produced, DNA encoding these phytases, methods of their production, as well as the use thereof, e.g. in animal feed and animal feed additives.

32 Claims, 9 Drawing Sheets

Fig. 1

```
Numbering                                           1         10        20
AEH25057    MTISAFNRKKLTLHPGLFVALSAIFSLGSTAYANDTPASGYQVEKVVILSRHGVRAPTKM
AEH25059    MTISAFNRKKLTLHPGLFVALSAIFSLGSTAYANDTPASGYQVEKVVILSRHGVRAPTKM
AEH25058    MTISAFNRKKLTLHPGLFVALSAIFSLGSTAYANDTPASGYQVEKVVILSRHGVRAPTKM
AEH25067    MTISAFNRKKLTLHPGLFVALSAIFSLGSTAYANDTPASGYQVEKVVILSRHGVRAPTKM
AEH25071    MTISAFNRKKLTLHPGLFVALSAIFSLGSTAYANDTPASGYQVEKVVILSRHGVRAPTKM
AEH25072    MTISAFNRKKLTLHPGLFVALSAIFSLGSTAYANDTPASGYQVEKVVILSRHGVRAPTKM
AEH25074    MTISAFNRKKLTLHPGLFVALSAIFSLGSTAYANDTPASGYQVEKVVILSRHGVRAPTKM
AEH25076    MTISAFNRKKLTLHPGLFVALSAIFSLGSTAYANDTPASGYQVEKVVILSRHGVRAPTKM
AEH25075    MTISAFNRKKLTLHPGLFVALSAIFSLGSTAYANDTPASGYQVEKVVILSRHGVRAPTKM
AEH25073    MTISAFNRKKLTLHPGLFVALSAIFSLGSTAYANDTPASGYQVEKVVILSRHGVRAPTKM
AEH25070    MTISAFNRKKLTLHPGLFVALSAIFSLGSTAYANDTPASGYQVEKVVILSRHGVRAPTKM
AEH25069    MTISAFNRKKLTLHPGLFVALSAIFSLGSTAYANDTPASGYQVEKVVILSRHGVRAPTKM
AEH25066    MTISAFNRKKLTLHPGLFVALSAIFSLGSTAYANDTPASGYQVEKVVILSRHGVRAPTKM
AEH25060    MTISAFNRKKLTLHPGLFVALSAIFSLGSTAYANDTPASGYQVEKVVILSRHGVRAPTKM
AEH25068    MTISAFNRKKLTLHPGLFVALSAIFSLGSTAYANDTPASGYQVEKVVILSRHGVRAPTKM
AEH25063    MTISAFNRKKLTLHPGLFVALSAIFSLGSTAYANDTPASGYQVEKVVILSRHGVRAPTKM
AEH25065    MTISAFNRKKLTLHPGLFVALSAIFSLGSTAYANDTPASGYQVEKVVILSRHGVRAPTKM
AEH25062    MTISAFNRKKLTLHPGLFVALSAIFSLGSTAYANDTPASGYQVEKVVILSRHGVRAPTKM
AEH25061    MTISAFNRKKLTLHPGLFVALSAIFSLGSTAYANDTPASGYQVEKVVILSRHGVRAPTKM
AEH25056    MTISAFNRKKLTLHPGLFVALSAIFSLGSTAYANDTPASGYQVEKVVILSRHGVRAPTEM
AEH25051    MTISAFNRKKLTLHPGLFVALSAIFSLGSTAYANDTPASGYQVEKVVILSRHGVRAPTKM
AEH25064    MTISAFNRKKLTLHPGLFVALSAIFSLGSTAYANDTPASGYQVEKVVILSRHGVRAPTKM
SEQ4        ----------------------FSLGLTAYASDTPASGYQIEKVVILSRHGVRAPTKM
SEQ6        MTFSAFNRKKLTLHPGLFVALSAIFSLGSTAYANDTPASGYQVEKVVILSRHGVRAPTKM
SEQ2        MTISAFNHKKLTLHPGLFVALSAIFSLGSTAYANDTPASGYQVEKVVILSRHGVRAPTKM
             .*******:*****************
```

Fig. 1 - continued

```
Numbering      30        40        50        60        70        80
AEH25057   TQTMRDVTPNTWPEWPVKLGYITPRGEHLISLMGGFYRQKFQQQGILSQGSCPTPNSIYV
AEH25059   TQTMRDVTPNTWPEWPVKLGYITPRGEHLISLMGGFYRQKFQQQGILSQGSCPTPNSIYV
AEH25058   TQTMRDVTPNTWPEWPVKLGYITPRGEHLISLMGGFYRQKFQQQGILSQGSCPTPNSIYV
AEH25067   TQTMRDVTPNTWPEWPVKLGYITPRGEHLISLMGGFYRQKFQQQGILSQGSCPTPNSIYV
AEH25071   TQTMRDVTPNTWPEWPVKLGYITPRGEHLISLMGGFYRQKFQQQGILSQGSCPTPNSIYV
AEH25072   TQTMRDVTPNTWPEWPVKLGYITPRGEHLISLMGGFYRQKFQQQGILSQGSCPTPNSIYV
AEH25074   TQTMRDVTPNTWPEWPVKLGYITPRGEHLISLMGGFYRQKFQQQGILSQGSCPTPNSIYV
AEH25076   TQTMRDVTPYTWPEWPVKLGYITPRGEHLISLMGGFYRQKFQQQGILSQGSCPTPNSIYV
AEH25075   TQTMRDVTPNTWPEWPVKLGYITPRGEHLISLMGGFYRQKFQQQGILSQGSCPTPNSIYV
AEH25073   TQTMRDVTPNTWPEWPVKLGYITPRGEHLISLMGGFYRQKFQQQGILSQGSCPTPNSIYV
AEH25070   TQTMRDVTPNTWPEWPVKLGYITPRGEHLISLMGGFYRQKFQQQGILSQGSCPTPNSIYV
AEH25069   TQTMRDVTPNTWPEWPVKLGYITPRGEHLISLMGGFYRQKFQQQGILSQGSCPTPNSIYV
AEH25066   TQTMRDVTPNTWPEWPVKLGYITPRGEHLISLMGGFYRQKFQQQGILSQGSCPTPNSIYV
AEH25060   TQTMRDVTPNTWPEWPVKLGYITPRGEHLISLMGGFYRQKFQQQGILSQGSCPTPNSIYV
AEH25068   TQTMRDVTPNTWPEWPVKLGYITPRGEHLISLMGGFYRQKFQQQGILSQGSCPTPNSIYV
AEH25063   TQTMRDVTPNTWPEWPVKLGYITPRGEHLISLMGGFYRQKFQQQGILSQGSCPTPNSIYV
AEH25065   TQTMRDVTPNTWPEWPVKLGYITPRGEHLISLMGGFYRQKFQQQGILSQGSCPTPNSIYV
AEH25062   TQTMRDVTPNTWPEWPVKLGYITPRGEHLISLMGGFYRQKFQQQGILSQGSCPTPNSIYV
AEH25061   TQTMRDVTPNTWPEWPVKLGYITPRGEHLISLMGGFYRQKFQQQGILSQGSCPTPNSIYV
AEH25056   TQTMRDVTPNTWPEWPVKLGYITPRGEHLISLMGGFYRQKFQQQGILSQGSCPTPNSIYV
AEH25051   TQTMRDVTPNTWPEWPVKLGYITPRGEHLISLMGGFYRQKFQQQGILSQGSCPTPNSIYV
AEH25064   TQTMRDVTPNTWPEWPVKLGYITPRGEHLISLMGGFYRQKFQQQGILSQGSCPTPNSIYV
SEQ4       TQTMRDVTPNSWPEWPVKLGYITPRGEHLISLMGGFYRQKFQQKGILSQGSCPTPNSIYV
SEQ6       TQTMRDVTPNTWPEWPVKLGYITPRGEHLISLMGGFYREKFQQQGILSQGSCPAPNSIYV
SEQ2       TQTMRDVTPNTWPEWPVKLGYITPRGEHLISLMGGFYREKFQQQGILSQGSCPTPNSIYV
           ********:*********************************:****:*********:******
```

Fig. 1 - continued

```
Numbering      90        100       110       120       130       140
AEH25057    WADVDQRTLKTGEAFLAGLAPECHLTIHHQQDIKKADPLFHPVKAGVCSMDKTQVQQAVE
AEH25059    WADVDQRTLKTGEAFLAGLAPECHLTIHHQQDIKKADPLFHPVKAGICSMDKTQVQQAVE
AEH25058    WADVDQRTLKTGEAFLAGLAPECHLTIHHQQDIKKADPLFHPVKAGTCSMDKTQVQQAVE
AEH25067    WADVDQRTLKTGEAFLAGLAPECHLTIHHQQDIKKADPLFHPVKAGICSMDKTQVQQAVE
AEH25071    WTDVDQRTLKTGEAFLAGLAPECHLTIHHQQDIKKADPLFHPVKAGICSMDKTQVQQAVE
AEH25072    WTDVDQRTLKTGEAFLAGLAPECHLTIHHQQDIKKADPLFHPVKAGICSMDKTQVQQAVE
AEH25074    WADVEQRTLKTGEAFLAGLAPECHLTIHHQQDIKKADPLFHPVKAGICSMDKTQVQQAVE
AEH25076    WADVEQRTLKTGEAFLAGLAPECHLTIHHQQDIKKADPLFHPVKAGICSMDKTQVQQAVE
AEH25075    WTDVDQRTLKTGEAFLAGLAPECHLTIHHQQDIKKADPLFHPVKAGICSMDKTQVQQAVE
AEH25073    WTDVEQRTLKTGEAFLAGLAPECHLTIHHQQDIKKADPLFHPVKAGTCSMDKTQVQQAVE
AEH25070    WADVDQRTLKTGEAFLAGLAPECHLTIHHQQDIKKADPLFHPVKAGICSMDKTQVQQAVE
AEH25069    WADVDQRTLKTGEAFLAGLAPECHLTIHHQQDIKKADPLFHPVKAGICSMDKTQVQQAVE
AEH25066    WADVDQRTLKTGEAFLAGLAPECHLTIHHQQDIKKADPLFHPVKAGTCSMDKTQVQQAVE
AEH25060    WADVDQRTLKTGEAFLAGLAPECHLTIHHQQDIKKADPLFHPVKAGTCSMDKTQVQQAVE
AEH25068    WADVDQRTLKTGEAFLAGLAPECHLTIHHQQDIKKADPLFHPVKAGTCSMDKTQVQQAVE
AEH25063    WADVDQRTLKTGEAFLAGLAPECHLTIHHQQDIKKADPLFHPVKAGTCSMDKTQVQQAVE
AEH25065    WADVEQRTLKTGEAFLAGLAPECHLTIHHQQDIKKADPLFHPVKAGTCSMDKTQVQQAVE
AEH25062    WADVDQRTLKTGEAFLAGLAPECHLTIHHQQDIKKADPLFHPVKAGTCSMDKTQVQQAVE
AEH25061    WADVDQRTLKTGEAFLAGLAPECHLTIHHQQDIKKADPLFHPVKAGTCSMDKTQVQQAVE
AEH25056    WADVDQRTLKTGEAFLAGLAPECHLTIHHQQDIKKADPLFHPVKAGTCSMDKTQVQQAVE
AEH25051    WADVDQRTLKTGEAFLAGLAPECHLTIHHQQDIKKADPLFHPVKAGTCSMDKTQVQQAVE
AEH25064    WADVDQRTLKTGEAFLAGLAPECHLTIHHQQDIKKADPLFHPVKAGTCSMDKTQVQQAVE
SEQ4        WADVDQRTLKTGEAFLAGLAPQCGLTIHHQQNLEKADPLFHPVKAGTCSMDKTQVQQAVE
SEQ6        WADVDQRTLKTGEAFLAGLAPQCGLTIHHQQNLEKADPLFHPVKAGTCSMDKTQVQQAVE
SEQ2        WADVDQRTLKTGEAFLAGLAPQCGLTIHHQQNLEKADPLFHPVKAGTCSMDKTRLQQAVE
            *:**:***************:* ******:::***********  *****::****
```

Fig. 1- continued

```
Numbering       150       160       170       180       190       200
AEH25057     KEAQTPIDNLNQHYIPFLALMNTTLNFSTSAWCQKHSADKSCDLGLSMPSKLSIKDNGNK
AEH25059     KEAQTPIDNLNQHYIPFLALMNTTLNFSTSAWCQKHSADKSCDLGLSMPSKLSIKDNGNK
AEH25058     KEAQTPIDNLNQHYIPFLALMNTTLNFSTSAWCQKHSADKSCDLGLSMPSKLSIKDNGNT
AEH25067     KEAQTPIDNLNQHYIPFLALMNTTLNFSTSAWCQKHSADKSCDLGLSMPSKLSIKDNGNT
AEH25071     KEAQTPIDNLNQHYIPSLALMNTTLNFSKSPWCQKHSADKSCDLGLSMPSKLSIKDNGNE
AEH25072     KEAQTPIDNLNQHYIPSLALMNTTLNFSKSPWCQKHSADKSCDLGLSMPSKLSIKDNGNE
AEH25074     KEAQTPIDNLNQRYIPSLALMNTILNFSKSPWCQKHSADKSCDLGLSMPSKLSIKDNGNE
AEH25076     KEAQTPIDNLNQRYIPSLALMNTILNFSKSPWCQKHSADKSCDLGLSMPSKLSIKDNGNE
AEH25075     KEAQTPIDNLNQRYIPSLALMNTILNFSKSPWCQKHSADKSCDLGLSMPSKLSIKDNGNE
AEH25073     KEAQTPIDNLNQRYIPSLALMNTTLNFSKSPWCQKHSADKNCDLALSMPSKLSIKDNGNE
AEH25070     KEAQTPIDNLNQHYIPFLALMNTTLNFSTSAWCQKHSADKSCDLGLSMPSKLSIKDNGNE
AEH25069     KEAQTPIDNLNQHYIPFLALMNTTLNFSTSAWCQKHSADKSCDLGLSMPSKLSIKDNGNT
AEH25066     KEAQTPIDNLNQHYIPFLALMNTTLNFSTSAWCQKHSADKSCDLGLSMPSKLSIKDNGNK
AEH25060     KEAQTPIDNLNQHYIPFLALMNTTLNFSTSAWCQKHSADKSCDLGLSMPSKLSIKDNGNE
AEH25068     KEAQTPIDNLNQHYIPFLALMNTTLNFSTSAWCQKHSADKSCELGLSMPSKLSIKDNGNE
AEH25063     KEAQTPIDNLNQHYIPFLALMNTTLNFSKSAWCQKHSADKSCDLGLSMPSKLSIKDNGNK
AEH25065     KEAQTPIDNLNQRYIPFLALMNTTLNFSTSAWCQKHSADKSCDLGLSMPSKLSIKDNGNK
AEH25062     KEAQTPIDNLNQHYIPFLALMNTTLNFSTSAWCQKHSADKSCDLGLSMPSKLSIKDNGNK
AEH25061     KEAQTPIDNLNQHYIPFLALMNTTLNFSTSAWCQKHSADKSCDLGLSMPSKLSIKDNGNK
AEH25056     KEAQTPIDNLNQHYIPFLALMNTTLNFSTSAWCQKHSADKSCDLGLSMPSKLSIKDNGNK
AEH25051     KEAQTPIDNLNQHYIPFLALMNTTLNFSTSAWCQKHSADKSCDLGLSMPSKLSIKDNGNK
AEH25064     KEAQTPIDNLNQHYIPSLALMNTTLNFSTSAWCQKHSADKSCDLGLSMPSKLSIKDNGNK
SEQ4         KEAQMPIENLNQHYIPSLALMNTTLNFSTSAWCQKHSADKSCDLAQSMPSKLSIKDNGNK
SEQ6         KEAQTPIDNLNQHYIPSLALMNTTLNFSTSAWCQKHSADKSCDLAQSMPSKLSIKDNGNK
SEQ2         KEAQTPIENLNQHYIPSLALMNTTLNFSTSAWCQKHSADKSCDLAQSMPSKLSIKDNGNK
             **** **:****:*** ****** ****.*.*********.*:*. *************
```

Fig. 1 - continued

```
Numbering       210        220        230        240        250        260
AEH25057   VALDGAIGLSSTLAEIFLLEYAQGMPQAAWGNIHSEQEWASLLKLHNVQFDLMARTPYIA
AEH25059   VALDGAIGLSSTLAEIFLLEYAQGMPQAAWGNIHSEQEWASLLKLHNVQFDLMARTPYIA
AEH25058   VALDGAIGLSSTLAEIFLLEYAQGMPQAAWGNIHSEQEWASLLKLHNVQFDLMARTPYIA
AEH25067   VALDGAIGLSSTLAEIFLLEYAQGMPQAAWGNIHSEQEWASLLKLHNVQFDLMARTPYIA
AEH25071   VALDGAIGLSSTLAEIFLLEYAQGMPQAAWGNIHSEQEWASLLKLHNVQFDLMERTPYIA
AEH25072   VSLDGAIGLSSTLAEIFLLEYAQGMPQAAWGNIHSEQEWALLLKLHNVYFDLMERTPYIA
AEH25074   VALDGAIGLSSTLAEIFLLEYAQGMPQVAWGNIHSEQEWASLLKLHNVHFDLMERTPYIA
AEH25076   VALDGAIGLSSTLAEIFLLEYAQGMPQVAWGNIHSEQEWASLLKLHNVHFDLMERTPYIA
AEH25075   VALDGAIGLSSTLAEIFLLEYAQGMPQVAWGNIHSEQEWASLLKLHNVHFDLMERTPYIA
AEH25073   VALDGAIGLSSTLAEIFLLEYAQGMPQAAWGNIHSEQEWASLLKLHNVQFDLMERTPYIA
AEH25070   VSLDGAIGLSSTLAEIFLLEYAQGMPQAAWGNIHSEQEWASLLKLHNVQFDLMERTPYIA
AEH25069   VALDGAIGLSSTLAEIFLLEYAQGMPQAAWGNIHSEQEWASLLKLHNVQFDLMERTPYIA
AEH25066   VALDGAIGLSSTLAEIFLLEYAQGMPQAAWGNIHSEQEWASLLKLHNVQFDLMERTPYIA
AEH25060   VALDGAIGLSSTLAEIFLLEYAQGMPQAAWGNIHSEQEWASLLKLHNVQFDLMARTPYIA
AEH25068   VALDGAIGLSSTLAEIFLLEYAQGMPQAAWGNIHSEQEWASLLKLHNVQFDLMARTPYIA
AEH25063   VALDGAIGLSSTLAEIFLLEYAQGMPQAAWGNIHSEQEWASLLKLHNVQFDLMARTPYIA
AEH25065   VALDGAIGLSSTLAEIFLLEYAQGMPQAAWGNIHSEQEWASLLKLHNVQFDLMARTPYIA
AEH25062   VALDGAIGLSSTLAEIFLLEYAQGMPQAAWGNIHSEQEWASLLKLHNVYFDLMARTPYIA
AEH25061   VALCGAIGLSSTLAEIFLLEYAQGMPQAAWGNIHSEQEWASLLKLHNVQFDLMARTPYIA
AEH25056   VALDGAIGLSSTLAEIFLLEYAQGMPQAAWGNIHSEQEWASLLKLHNVQFDLMARTPYIA
AEH25051   VALDGAIGLSSTLAEIFLLEYAQGMPQAAWGNIHSEQEWASLLKLHNVQFDLMARTPYIA
AEH25064   VALDGAIGLSSTLAEIFLLEYAQGMPQAAWGNIHSEQEWASLLKLHNVQFDLMARTPYIA
SEQ4       VALDGAIGLSSTLAEIFLLEYAQGMPQAAWGNIHSEQEWASLLKLHNTQFDLMARTPYIA
SEQ6       VALDGAIGLSSTLAEIFLLEYAQGMPQAAWGNIHSEQEWASLLKLHNAQFDLMARTPYIA
SEQ2       VALDGAVGLSSTLAEIFLLEYAQGMPQAAWGKIHSEQDWAELLKLHNAQFDLMARTPYIA
           *:*  **:******************.***:*****:** ******. **** ******
```

Fig. 1- continued

```
Numbering       270       280       290       300       310       320
AEH25057    RHNGTPLLQAISNALNPNATESKLPDISPDNKILFIAGHDTNIANIAGMLNMRWTLPGQP
AEH25059    RHNGTPLLQAISNALNPNATESKLPDISPDNKILFIAGHDTNIANIAGMLNMRWTLPGQP
AEH25058    RHNGTPLLQAISNALNPNATESKLPDISPDNKILFIAGHDTNIANIAGMLNMRWTLPGQP
AEH25067    RHNGTPLLQAISNALNPNATESKLPDISPDNKILFIAGHDTNIANIAGMLNMRWTLPGQP
AEH25071    RHKGTPLLQAISNALNPNATESKLPDISPDNKILFIAGHDTNIANIAGMLNMRWTLPGQP
AEH25072    RHKGTPLLQAISNALNPNATESKLPDISPDNKILFIAGHDTNIANIAGMLNMRWTLPGQP
AEH25074    RHKGTPLLQAISNALNPNATESKLPDISPDNKILFIAGHDTNIANIAGMLNMRWTLPGQP
AEH25076    RHKGTPLLQAISNALNPNATESKLPDISPDNKILFIAGHDTNIANIAGMLNMRWTLPGQP
AEH25075    RHKGTPLLQAISNALNPNATESKLPDISPDNKILFFAGHDTNIANIAGMLNMRWTLPGQP
AEH25073    RHKGTPLLQAISNALNPNATESKLPDISPDNKILFIAGHDTNIANIAGMLNMRWTLPGQP
AEH25070    RHKGTPLLQAISNALNPNATESKLPDISPDNKILFIAGHDTNIANIAGMLNMRWTLPGQP
AEH25069    RHKGTPLLQAISNALNPNATESKLPDISPDNKILFIAGHDTNIANIAGMLNMRWTLPGQP
AEH25066    RHKGTPLLQAISNALNPNATESKLPDISPDNKILFIAGHDTNIANIAGMLNMRWTLPGQP
AEH25060    RHNGTPLLQAISNALNPNATESKLPDISPDNKILFIAGHDTNIANIAGMLNMRWTLPGQP
AEH25068    RHNGTPLLQAISNALNPNATESKLPDISPDNKILFIAGHDTNIANIAGMLDMRWTLPGQP
AEH25063    RHNGTPLLQAISNALNPNATESKLPDISPDNKILFIAGHDTNIANIAGMLNMRWTLPGQP
AEH25065    RHNGTPLLQAISNALNPNATESKLPDISPDNKILFIAGHDTNIANIAGMLNMRWTLPGQP
AEH25062    RHNGTPLLQAISNALNPNATESKLPDISPDNKILFIAGHDTNIANIAGMLNMRWTLPGQP
AEH25061    RHNGTPLLQAISNALNPNATESKLPDISPDNKILFIAGHDTNIANIAGMLNMRWTLPGQP
AEH25056    RHNGTPLLQAISNALNPNATESKLPDISPDNKILFIAGHDTNIANIAGMLNMRWTLPGQP
AEH25051    RHNGTPLLQAISNALNPNATESKLPDISPDNKILFIAGHDTNIANIAGMLNMRWTLPGQP
AEH25064    RHNGTPLLQAISNALNPNATESKLPDISPDNKILFIAGHDTNIANIAGMLNMRWTLPGQP
SEQ4        AHNGTPLLQTISNALEPKADVSKLPDISSDNKILFIAGHDTNIANIAGMLNMRWTLPGQP
SEQ6        THNGTPLLQTISNALEPKADVSKLPGISPDNKILFLAGHDTNIANIAGMLNMRWTLPGQP
SEQ2        RHNGTPLLQAISNALDPNATASKLPDISPDNKILFIAGHDTNIANISGMLNMRWTLPGQP
            *:******:*****:*:*  ****.**.******:**********:***:*********
```

Fig. 1- continued

```
Numbering      330        340        350        360        370        380
AEH25057   DNTPPGGALVFERLADKSGKQYVSVSMVYQTLEQLRSQTPLSLNQPAGSVQLKIPGCNDQ
AEH25059   DNTPPGGALVFERLADKSGKQYVSVSMVYQTLEQLRSQTPLSLNQPAGSVQLKIPGCNDQ
AEH25058   DNTPPGGALVFERLADKSGKQYVSVSMVYQTLEQLRSQTPLSLNQPAGSVQLKIPGCNDQ
AEH25067   DNTPPGGALVFERLADKSGKQYVSVSMVYQTLEQLRSQTPLSLNQPAGSVQLKIPGCNDQ
AEH25071   DNTPPGGALVFERLADKSGKQYVSVSMVYQTLEQLRSQTPLSLNQPAGSVQLKIPGCNDQ
AEH25072   DNTPPGGALVFERLADKSGKQYVSVSMVYQTLEQLRSQTPLSLNQPAGSVQLKIPGCNDQ
AEH25074   DNTPPGGALVFERLADKSGKQYVSVSMVYQTLEQLRSQTPLSLNQPAGSVQLKIPGCNDQ
AEH25076   DNTPPGGALVFERLADKSGKQYVSVSMVYQTLEQLRSQTPLSLNQPAGSVQLKIPGCNDQ
AEH25075   DNTPPGGALVFERLADKSGKQYVSVSMVYQTLEQLRSQTPLSLNQPAGSVQLKIPGCNDQ
AEH25073   DNTPPGGALVFERLADKSGKQYVSVSMVYQTLEQLRSQTPLSLNQPAGSVQLKIPGCNDQ
AEH25070   DNTPPGGALVFERLADKSGKQYVSVSMVYQTLEQLRSQTPLSLNQPAGSVQLKIPGCNDQ
AEH25069   DNTPPGGALVFERLADKSGKQYVSVSMVYQTLEQLRSQTPLSLNQPAGSVQLKIPGCNDQ
AEH25066   DNTPPGGALVFERLADKSGKQYVSVSMVYQTLEQLRSQTPLSLNQPAGSVQLKIPGCNDQ
AEH25060   DNTPPGGALVFERLADKSGKQYVSVSMVYQTLEQLRSQTPLSLNQPAGSVQLKIPGCNDQ
AEH25068   DNTPPGGALVFERLADKSGKQYVSVSMVYQTLEQLRSQTPLSLNQPAGSVQLKIPGCNDQ
AEH25063   DNTPPGGALVFERLADKSGKQYVSVSMVYQTLEQLRSQTPLSLNQPAGSVQLKIPGCNDQ
AEH25065   DNTPPGGALVFERLADKSGKQYVSVSMVYQTLEQLRSQTPLSLNQPAGSVQLKIPGCNDQ
AEH25062   DNTPPGGALVFERLADKSGKQYVSVSMVYQTLEQLRSQTPLSLNQPAGSVQLKIPGCNDQ
AEH25061   DNTPPGGALVFERLADKSGKQYVSVSMVYQTLEQLRSQTPLSLNQPAGSVQLKIPGCNDQ
AEH25056   DNTPPGGALVFERLADKSGKQYVSVSMVYQTLEQLRSQTPLSLNQPAGSVQLKIPGCNDQ
AEH25051   DNTPPGGALVFERLADKSGKQYVSVSMVYQTLEQLRSQTPLSLNQPAGSVQLKIPGCNDQ
AEH25064   DNTPPGGALVFERLADKSGKQYVSVSMVYQTLEQLRSQTPLSLNQPAGSVQLKIPGCNDQ
SEQ4       DNTPPGGALVFERLADKSGKQYISVSMVYQTLEQLRAQTPLSLNEPAGSVQLKIPGCNDQ
SEQ6       DNTPPGGALVFERLADKSGKQYVSVSMVYQTLEQLRSQTPLSLNQPAGSVQLKIPGCNDQ
SEQ2       DNTPPGGALIFERLADKAGKQYVSVSMVYQTLEQLRAQTPLSLKEPAGSVQLKIPGCNDQ
           ********:*****.****:*************:******:::***************
```

Fig. 1- continued

```
Numbering     390       400       410
AEH25057    TAEGYCPLSTFTRVVSQSVEPGCQLQ
AEH25059    TAEGYCPLSTFTRVVSQSVEPGCQLQ
AEH25058    TAEGYCPLSTFTRVVSQSVEPGCQLQ
AEH25067    TAEGYCPLSTFTRVVSQSVEPGCQLQ
AEH25071    TAEGYCPLSTFTRVVSQSVEPGCQLQ
AEH25072    TAEGYCPLSTFTRVVSQSVEPGCQLQ
AEH25074    TAEGYCPLSTFTRVVSQSVEPGCQLQ
AEH25076    TAEGYCPLSTFTRVVSQSVEPGCQLQ
AEH25075    TAEGYCPLSTFTRVVSQSVEPGCQLQ
AEH25073    TAEGYCPLSTFTRVVSQSVEPGCQLQ
AEH25070    TAEGYCPLSTFTRVVSQSVEPGCQLQ
AEH25069    TAEGYCPLSTFTRVVSQSVEPGCQLQ
AEH25066    TAEGYCPLSTFTRVVSQSVEPGCQLQ
AEH25060    TAEGYCPLSTFTRVVSQSVEPGCQLQ
AEH25068    TAEGYCPLSTFTRVVSQSVEPGCQLQ
AEH25063    TAEGYCPLSTFTRVVSQSVEPGCQLQ
AEH25065    TAEGYCPLSTFTRVVSQSVEPGCQLQ
AEH25062    TAEGYCPLSTFTRVVSQSVEPGCQLQ
AEH25061    TAEGYCPLSTFTRVVSQSVEPGCQLQ
AEH25056    TAEGYCPLSTFTRVVSQSVEPGCQLQ
AEH25051    TAEGYCPLSTFTRVVSQSVEPGCQLQ
AEH25064    TAEGYCPLSTFTRVVSQSVEPGCQLQ
SEQ4        TAEGYCPLSTFTRVVSQSVEPGCQL*P*
SEQ6        TAEGYCPLSTFTRVVSQSVEPGCQLQ
SEQ2        TAEGYCPL*P*TF*K*RVVSQS*E*EPGCQLQ
            ********.**.****** ******
```

Fig. 2

```
Program: needle
Matrix: BLOSUM62
Gap initiation penalty: 10.0
Gap extension penalty: 0.5
Number of identical residues: 315
Length of shortest sequence: 413
% Identity: 315/413 = 76.3%
SEQ2_mature      1                                       NDTPASGYQVEKVVILS    17
                                                         ::|..||||:|||||||
UNIPROTQ6U677    1   MTISLFTHSPTRLLKCMPLAFIAASMLTTASYASETEPSGYQLEKVVILS    50
SEQ2_mature     18   RHGVRAPTKMTQTMRDVTPNTWPEWPVKLGYITPRGEHLISLMGGFYREK    67
                     ||||||||||||||||||||.||||||||||||||||||:|||||||:|
UNIPROTQ6U677   51   RHGVRAPTKMTQTMRDVTPNAWPEWPVKLGYITPRGEHLVSLMGGFYRQK   100
SEQ2_mature     68   FQQQGILSQGSCPTPNSIYVWADVDQRTLKTGEAFLAGLAPQCGLTIHHQ   117
                     |||.||||:|.||||.|.::||||||||||.|||||||||||:|.|:||||
UNIPROTQ6U677  101   FQQLGILSKGRCPTANDVYVWADVDQRTRKTGEAFLAGLAPECHLSIHHQ   150
SEQ2_mature    118   QNLEKADPLFHPVKAGTCSMDKTRLQQAVEKEAQTPIENLNQHYIPSLAL   167
                     |::::||||||||||.|:|:||::|||||::..||:.||||.|:|||
UNIPROTQ6U677  151   QDIKQADPLFHPVKAGVCTMEKTQVQQAVEQQAGMPIDQLNQHYRPALAL   200
SEQ2_mature    168   MNTTLNFSTSAWCQKHSADKSCDLAQSMPSKLSIKDNGNKVALDGAVGLS   217
                     |::.||...|.:||:|||::|||||::|||||||||||||||||||||
UNIPROTQ6U677  201   MSSVLNFPKSTYCQQHSADQTCDLAQAMPSKLSIKDNGNKVALDGAVGLS   250
SEQ2_mature    218   STLAEIFLLEYAQGMPQAAWGKIHSEQDWAELLKLHNAQFDLMARTPYIA   267
                     ||||||||||||||.|||||||||||...||.||||||||||:||||||
UNIPROTQ6U677  251   STLAEIFLLEYAQGMPDAAWGKIHSEQDWNALLTLHNAQFDLMSRTPYIA   300
SEQ2_mature    268   RHNGTPLLQAISNALDPNATASKLPDISPDNKILFIAGHDTNIANISGML   317
                     :||||||||.|.:|:...::.:||::|.||||||.|||||||||||:||.
UNIPROTQ6U677  301   KHNGTPLLQTIVSAINSQPSSRELPELSADNKILFPAGHDTNIANIAGMF   350
SEQ2_mature    318   NMRWTLPGQPDNTPPGGALIFERLADKAGKQYVSVSMVYQTLEQLRAQTP   367
                     .|.|.|||||||||||||:|||.:||.||:||||.|:||||.|||.|||
UNIPROTQ6U677  351   GMSWALPGQPDNTPPGGALVFERWSDKTGKKYVSVQMMYQTLAQLRNQTP   400
SEQ2_mature    368   LSLKEPAGSVQLKIPGCNDQTAEGYCPLPTFKRVVSQSEEPGCQLQ       413
                     |:|.:|||||.||||||:|||||||||||.||.|:...:|...||
UNIPROTQ6U677  401   LTLDKPAGSVALKIPGCDDQTAEGYCPLDTFTRLAKQNELVECQ         444
```

THERMOSTABLE PHYTASE VARIANTS

CROSS-REFERENCE TO RELATED APPLICATIONS

This application is a 35 U.S.C. 371 national application of PCT/EP2011/054640 filed Mar. 25, 2011, which claims priority or the benefit under 35 U.S.C. 119 of European application no. 10158026.4 filed Mar. 26, 2010 and U.S. provisional application no. 61/318,024 filed Mar. 26, 2010 the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method of producing a variant phytase from a parent phytase which has at least 70% identity to amino acids 1-413 of SEQ ID NO:2, amino acids 1-413 of SEQ ID NO:4, and/or amino acids 1-413 of SEQ ID NO:6 when aligned to the respective amino acid sequence using the Needle program with the BLOSUM62 substitution matrix, a gap opening penalty of 10.0, and a gap extension penalty of 0.5, and comprises the establishment of at least one disulfide bridge that is not among the four naturally occurring disulfide bridges as compared to these and closely related phytases (i.e., is a variant thereof). The invention also relates to the variants produced and DNA encoding these, as well as the use thereof, e.g. in animal feed and animal feed additives.

BACKGROUND OF THE INVENTION

Background Art

Phytases are well-known enzymes, as are the advantages of adding them to foodstuffs for animals, including humans. Phytases have been isolated from various sources, including a number of fungal and bacterial strains.

It is an object of the present invention to provide alternative polypeptides having phytase activity (phytases) and polynucleotides encoding the polypeptides. The phytase variants of the invention exhibit modified or altered preferably improved properties as compared to the parent phytase. Non-limiting examples of such properties are: Stability (such as acid-stability, heat-stability, steam stability, pelleting stability, and/or protease stability, in particular pepsin stability), temperature profile, pH profile, specific activity, substrate specificity, performance in animal feed (such as an improved release and/or degradation of phytate), susceptibility to glycation, and/or glycosylation pattern.

As described herein, mutagenesis of a parent polynucleotide encoding a phytase is employed to prepare variant (synthetic) DNAs encoding a phytase having improved properties relative to the phytase encoded by the parent polynucleotide.

A number of three-dimensional structures of phytases of the Histidine acid phosphate (HAP) type are known. (e.g. Lim et al. Nature struct. biol. 7, 108-113 (2000)). From these it has been found that they all have four disulfide bridges located at the position pairs 77/108 133/407 178/187 381/390 (according to the numbering used here). Typically these occupy all the cysteines present in the molecule.

Buttiauxiella

WO 2006/043178 discloses a phytase from Buttiauxella P1-29 (deposited as NCIMB 41248) having the amino acid sequence of SEQ ID NO:3 in WO 2006/043178, as well as certain variants thereof. The sequence of a Buttiauxella wild-type phytase and a number of variants thereof have been submitted to the GENESEQP database with the following accession numbers: AEH25051(SEQ ID NO: 7), AEH25056 (SEQ ID NO: 8), AEH25057(SEQ ID NO: 9), AEH25058 (SEQ ID NO: 10), AEH25059(SEQ ID NO: 11), AEH25060 (SEQ ID NO: 12), AEH25061(SEQ ID NO: 13), AEH25062 (SEQ ID NO: 14), AEH25063(SEQ ID NO: 15), AEH25064 (SEQ ID NO:16), AEH25065(SEQ ID NO: 17), AEH25066 (SEQ ID NO: 18), AEH25067(SEQ ID NO: 19), AEH25068 (SEQ ID NO: 20), AEH25069(SEQ ID NO: 21), AEH25070 (SEQ ID NO: 22), AEH25071(SEQ ID NO: 23), AEH25072 (SEQ ID NO: 24), AEH25073(SEQ ID NO: 25), AEH25074 (SEQ ID NO: 26), AEH25075(SEQ ID NO: 27), and AEH25076(SEQ ID NO: 28). These phytases all have a percentage of identity to any one of SEQ ID NOs:2, 4 and 6 of above 70%.

The sequence of a phytase from Obesumbacterium proteus has been submitted to the UNIPROT database with accession number Q6U677 (SEQ ID NO: 29). This phytase, which is also described by Zinin et al in FEMS Microbiology Letters, vol. 236, pp. 283-290, 2004, has a percentage of identity to SEQ ID NOs:2, 4 and 6 of above 70%.

WO 2008/192901 discloses phytases from Buttiauxella gaviniae DSM18930, Buttiauxella agrestis DSM18931, and Buttiauxella agrestis DSM18932 and a number of variants thereof. These phytases are provided in SEQ ID NO:2, SEQ ID NO:4 and SEQ ID NO:6 herein.

WO2008/097619 discloses also phytase variants derived from Buttiauxella sp strain P 1-29, especially the variant designated BP-11 and some variants thereof.

WO 2009/100183 discloses further variants derived from Buttiauxella sp P1-29 phytase or the BP-11 variant.

BRIEF DESCRIPTION OF THE DRAWINGS AND SEQUENCE LISTING

FIG. 1 shows a multiple alignment of the expected mature parts of SEQ ID NO:2, SEQ ID NO:4 and SEQ ID NO:6 together with the sequences with the following GENESEQP accession numbers: AEH25051(SEQ ID NO: 7), AEH25056 (SEQ ID NO: 8), AEH25057(SEQ ID NO: 9), AEH25058 (SEQ ID NO: 10), AEH25059(SEQ ID NO: 11), AEH25060 (SEQ ID NO: 12), AEH25061(SEQ ID NO: 13), AEH25062 (SEQ ID NO: 14), AEH25063(SEQ ID NO: 15), AEH25064 (SEQ ID NO: 16), AEH25065(SEQ ID NO: 17), AEH25066 (SEQ ID NO: 18), AEH25067(SEQ ID NO: 19), AEH25068 (SEQ ID NO: 20), AEH25069(SEQ ID NO: 21), AEH25070 (SEQ ID NO: 22), AEH25071(SEQ ID NO: 23), AEH25072 (SEQ ID NO: 24), AEH25073(SEQ ID NO: 25), AEH25074 (SEQ ID NO: 26), AEH25075(SEQ ID NO: 27), and AEH25076(SEQ ID NO: 28). The alignment was made using the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

FIG. 2 shows an alignment of UNIPROT accession no. Q6U677 (SEQ ID NO: 29) with amino acids 1-413 of SEQ ID NO:2. The alignment was made using the program needle with the matrix BLOSUM62, a gap initiation penalty of 10.0 and a gap extension penalty of 0.5.

In the Sequence listing the sequences apply as follows:

| | |
|---|---|
| SEQ ID NO: 1 | *Buttiauxella gaviniae* DSM18930 |
| SEQ ID NO: 2 | *Buttiauxella gaviniae* DSM18930 |
| SEQ ID NO: 3 | *Buttiauxella agrestis* DSM18931 |
| SEQ ID NO: 4 | *Buttiauxella agrestis* DSM18931 |
| SEQ ID NO: 5 | *Buttiauxella agrestis* DSM18932 |
| SEQ ID NO: 6 | *Buttiauxella agrestis* DSM18932 |

SUMMARY OF EXAMPLES

In the specification the following examples are provided:
Example 1: Preparation of variants, and determination of activity
Example 2: Specific activity
Example 3: Thermostability by DSC
Example 4: Temperature profile
Example 5: Performance in animal feed in an in vitro model
Example 6: Performance in an in vivo pig trial Description of The Invention The present invention relates to a method of producing a variant phytase from a parent phytase which
a) has at least 70% identity to amino acids 1-413 of SEQ ID NO:2, amino acids 1-413 of SEQ ID NO:4, and/or amino acids 1-413 of SEQ ID NO:6 when aligned to the respective amino acid sequence using the Needle program with the BLOSUM62 substitution matrix, a gap opening penalty of 10.0, and a gap extension penalty of 0.5; and
b) comprises the establishment of at least one disulfide bridge as compared to SEQ ID NO:2,
wherein said disulfide bridge is not among the four naturally occurring ones in positions 79/110, 135/410, 180/189, and 384/393

The percentage of identity is determined as described in the section "Phytase Polypeptides, Percentage of Identity".

The position numbers refer to the position numbering of SEQ ID NO:2, as described in the section "Position Numbering." Positions corresponding to these SEQ ID NO:2 position numbers in other phytases are determined as described in the section "Identifying Corresponding Position Numbers."

The at least one disulfide bridge is established in one or more positions selected from the group consisting of the position pairs: A) 143C/201C, B) 33C/179C, C) 54C/101C, D) 93C/48C, E) 33C/178C, F) 61C/102C, and G) 164C/251C.

According to the invention a first disulfide bridge is preferably established in the position pair A between the residues in positions 143 and 201 and a second disulfide bridge is established in the position pair B between the residues in positions 33 and 179.

In certain embodiments the number of established disulfide bridges is 2, 3, 4, 5, 6 and/or 7.

When the number of established disulfide bridges is two the following combinations of position pairs may be created: A+B, A+C, A+D, A+E, A+F, A+G, B+C, B+D, B+E, B+F, B+G, C+D, C+E, C+F, C+G, D+E, D+F, D+G, E+F, E+G, and F+G.

When the number of established disulfide bridges is three the following combinations of position pairs may be created: A+B+C, A+B+D, A+B+E, A+B+F, A+B+G, A+C+D, A+C+E, A+C+F, A+C+G, A+D+E, A+D+F, A+D+G, A+E+F, A+E+G, A+F+G, B+C+D, B+C+E, B+C+F, B+C+G, B+D+E, B+D+F, B+D+G, B+E+F, B+E+G, B+F+G, C+D+E, C+D+F, C+D+G, C+E+F, C+E+G, C+F+G, D+E+F, D+E+G, D+F+G, and E+F+G.

When the number of established disulfide bridges is four the following combinations of position pairs may be created: A+B+C+D, A+B+C+E, A+B+C+F, A+B+C+G, A+B+D+E, A+B+D+F, A+B+D+G, A+B+E+F, A+B+E+G, A+B+F+G, A+C+D+E, A+C+D+F, A+C+D+G, A+C+E+F, A+C+E+G, A+C+E+H, A+C+F+G, A+D+E+F, A+D+E+G, A+D+F+G, A+E+F+G, B+C+D+E, B+C+D+F, B+C+D+G, B+C+E+F, B+C+E+G, B+C+F+G, B+D+E+F, B+D+E+G, B+D+F+G, B+E+F+G, C+D+E+F, C+D+E+G, C+D+F+G, C+E+F+G, C+E+F+H, and D+E+F+G.

When the number of established disulfide bridges is five the following combinations of position pairs may be created: A+B+C+D+E, A+B+C+D+F, A+B+C+D+G, A+B+C+E+F, A+B+C+E+G, A+B+C+F+G, A+B+D+E+F, A+B+D+E+G, A+B+D+F+G, A+B+E+F+G, A+B+F+G+H, A+C+D+E+F, A+C+D+E+G, A+C+D+F+G, A+C+E+F+G, A+D+E+F+G, B+C+D+E+F, B+C+D+E+G, B+C+D+F+G, B+C+E+F+G, B+D+E+F+G, and C+D+E+F+G.

When the number of established disulfide bridges is six the following combinations of position pairs may be created: A+B+C+D+E+F, A+B+C+D+E+G, A+B+C+D+F+G, A+B+C+E+F+G, A+B+D+E+F+G, A+C+D+E+F+G, and B+C+D+E+F+G.

When the number of established disulfide bridges is seven the following combination of position pairs may be created: A+B+C+D+E+F+G.

In all of the above combinations A means 143C/201C, B means 33C/179C, C means 54C/101C, D means 93C/48C, E means 33C/178C, F means 61C/102C, and G means 164C/251C According to the method of the invention the phytase variant may further comprise at least one modification in at least one position selected from the following: 1, 9, 10, 18, 22, 25, 26, 37, 38, 66, 71, 81, 89, 92, 94, 109, 111, 119, 120, 121, 131, 134, 141, 142, 144, 152, 155, 160, 164, 171, 176, 178, 188, 190, 192, 193, 206, 207, 209, 211, 214, 215, 219, 222, 239, 235, 243, 245, 248, 253, 255, 256, 257, 260, 261, 268, 270, 277, 283, 285, 287, 288, 293, 296, 303, 306, 307, 308, 314, 318, 328, 337, 345, 350, 364, 371, 372, 396, 399, 406, and/or 413.

The invention further provides that the above modifications specifically are chosen from the following modifications: 1S, 9I, 10I, R18, R22, T25, 26E, 37Y, 38S, 66E, 71K, 81A, 89T, 92E, R94, 109Q, 111G, 119N, 120L, 121E, K131, 134I, 134V, 141R, 142L, T144, 152M, 155E, 160R, 164F, 171I, 176K, 178P, 188N, 190E, 192G, 193Q, N206, 207E, 207T, 209S, 211C, 214V, G215, T219, E222, 239K, 235V, E243, 245D, 248E, 248L, 248S, H253, 255A, 255T, 256H, 256Y, F257, M260, 261E, 268A, 268T, 270K, 277T, 283E, 283D, 285K, 287D, 288V, 288A, 293G, 296S, 303L, 303F, H306, D307, T308, 314A, 314S, 318D, D328, 337I, 345A, 350I, 364A, 371K, 372E, 396P, 399K, 406E, and/or 413P.

In specific embodiments of the invention the additional disulfide bridges are selected from the group comprising: Q143C/I201C, D33C/W179C, E54C/A101C, Q93C/Y48C, D33C/A178C, G61C/F102C, and F164C/K251C.

In further specific embodiments of the method of the invention further specific modifications are: N1S, S1N, I9V, V9I, V10I, K26E, N37Y, T38S, S38T, E66Q, Q66E, K71Q, Q71K, T81A, A81T, A89T, D92E, E109Q, H111G, D119N, I120L, K121E, T134I, T134V, R141Q, Q141R, V142L, L142V, T144I, T152M, M152T, E155D, D155E, H160R, S164F, F164S, T171I, T176K, A178P, S188N, D190E, A192G, G192A, L193Q, K207E, K207T, A209S, D211C, I214V, V214I, A235V, K239N, N239K, E245D, D245E, E248S, E248L, S248L, S248E, A255T, T255A, V255A, V255T, Q256H, Q256Y, A261E, R268A, R268T, A268R, A268T, T268A, T268R, N270K, A277T, T277A, D283N, D283E, E283N, E283D, N283D, N283E, N285K, K285N, D287T, T287D, A288E, A288V, V288E, V288A, E288A, E288V, D293G, P296S, S296P, I303L, I303F, L303F, F303L, L303I, S314A, A314S, N318D, I337V, V337I, S345A, A345S, V350I, I350V, A364S, A364S, S364A, K371N, N371K, E372Q, E372Q, Q372E, P396S, S396P, T399K, K399T, E406V, V406E, P413Q and/or Q413P and/or from the following combinations D92E/H160R, A261 E/N270K, T134I/K207T, D190E/K207E/N318D, T134I/K207T/A261E/N270K, T134I/K207E/A209S/A261E/N270K, A89T/T134I/F164S/T176K/A178P/K207E/A261E/N270K, A89T/T134I/F164S/T176K/A178P/K207E/A209S/S248L/Q256Y/A261E/N270K, A89T/D92E/H160R/F164S/T176K/A178P/S188N/G192A/K207E/A261E/N270K, D92E/T134I/H160R/F164S/T170I/T176K/A188P/K207E/A235V/Q256H/A261E/N270K, A89T/T134I/H160R/F164S/T170I/T176K/A188P/K207E/A235V/Q256H/A261E/N270K/I303F, and/or N37Y/D92E/T134I/H160R/F164S/T171I/T176K/A188P/K207E/A235V/Q256H/A261E/N270K.

The method of the invention may be used to create a variant of any wildtype or variant phytase. In particular embodiments, it produces a variant of the mature part of the phytase of SEQ ID NO:2, SEQ ID NO:4, or SEQ ID NO:6, or a mature part of any one of the following GENESEQP sequences: AEH25051, AEH25056, AEH25057, AEH25058, AEH25059, AEH25060, AEH25061, AEH25062, AEH25063, AEH25064, AEH25065, AEH25066, AEH25067, AEH25068, AEH25069, AEH25070, AEH25071, AEH25072, AEH25073, AEH25074, AEH25075, or AEH25076 that is used as a parent/backbone for producing a phytase variant.

The method of the invention may provide a phytase variant having improved properties, such as thermostability, heat-stability, steam stability, temperature profile, pelleting stability, acid-stability, pH profile, and/or protease stability, in particular pepsin stability, specific activity, substrate specificity, performance in animal feed (such as an improved release and/or degradation of phytate), susceptibility to glycation, and/or glycosylation pattern. The variants provided by the invention exhibit especially improved thermal properties, such as thermostability, heat-stability, steam stability, temperature profile, pelleting stability or improved performance in animal feed.

The method of the invention thus relates to phytase variants having improved thermal properties, such as thermostability, heat-stability, steam stability, temperature profile, and/or pelleting stability.

The method of the invention thus relates to phytase variants having improved thermostability.

The method of the invention thus relates to phytase variants having improved heat-stability.

The method of the invention thus relates to phytase variants having improved steam stability.

The method of the invention thus relates to phytase variants having improved temperature profile.

The method of the invention thus relates to phytase variants having improved pelleting stability.

The method of the invention thus relates to phytase variants having improved acid-stability.

The method of the invention thus relates to phytase variants having improved pH profile.

The method of the invention thus relates to phytase variants having improved protease stability, in particular pepsin stability.

The method of the invention thus relates to phytase variants having improved specific activity.

The method of the invention thus relates to phytase variants having improved substrate specificity.

The method of the invention thus relates to phytase variants having improved performance in animal feed (such as an improved release and/or degradation of phytate).

The method of the invention thus relates to phytase variants having improved susceptibility to glycation.

The method of the invention thus relates to phytase variants having improved and/or glycosylation pattern.

The invention further relates to polynucleotide comprising nucleotide sequences which encode the phytase variants produced by the method, nucleic acid constructs comprising the polynucleotides operably linked to one or more control sequences that direct the production of the polypeptide in an expression host, recombinant expression vectors comprising such nucleic acid constructs, and recombinant host cells comprising a nucleic acid construct and/or an expression vector.

The invention further relates to methods for producing phytase variants as provided comprising
(a) cultivating a host cell to produce a supernatant comprising the phytase; and
(b) recovering the phytase.

The invention further relates to transgenic plants, or plant part, capable of expressing the phytase variants, compositions comprising at least one phytase variant, and (a) at least one fat soluble vitamin; (b) at least one water soluble vitamin; and/or (c) at least one trace mineral. Such compositions may further comprise at least one enzyme selected from the following group of enzymes: amylase, phytase, phosphatase, xylanase, galactanase, alpha-galactosidase, protease, phospholipase, and/or beta-glucanase. the compositions may be animal feed additives that may have a crude protein content of 50 to 800 g/kg and comprising a phytase variant of the invention.

The invention further relates to methods for improving the nutritional value of an animal feed, by adding a phytase variant of the invention to the feed, processes for reducing phytate levels in animal manure by feeding an animal with an effective amount of the feed, methods for the treatment of vegetable proteins, comprising the step of adding a phytase variant to at least one vegetable protein, and the use of a phytase variant of a composition of the invention.

The invention also provides a method for producing a fermentation product such as, e.g., ethanol, beer, wine, comprising fermenting a carbohydrate material in the presence of a phytase variant, a method for producing ethanol comprising fermenting a carbohydrate material in the presence of a phytase variant and producing ethanol.

Phytase Polypeptides, Percentage of Identity

In the present context a phytase is a polypeptide having phytase activity, i.e. an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

In the present context the term a phytase substrate encompasses, i.a., phytic acid and any phytate (salt of phytic acid), as well as the phosphates listed under (2) above.

The ENZYME site at the internet (www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

According to the ENZYME site, three different types of phytases are known: A so-called 3-phytase (alternative name 1-phytase; a myo-inositol hexaphosphate 3-phosphohydrolase, EC 3.1.3.8), a so-called 4-phytase (alternative name 6-phytase, name based on 1L-numbering system and not 1D-numbering, EC 3.1.3.26), and a so-called 5-phytase (EC 3.1.3.72). For the purposes of the present invention, all three types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 16 to 22 of SEQ ID NOs:2, 3, 4, 6 and amino acids 38-44 of SEQ ID NO:9). In a preferred embodiment, the conserved active site motif is R-H-G-V-R-A-P, i.e. amino acids 16-22 (by reference to SEQ ID NO:2) are RHGVRAP.

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the assays of Example 1 ("Determination of phosphatase activity" or "Determination of phytase activity").

In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

The relatedness between two amino acid sequences is described by the parameter "identity". For purposes of the present invention, the alignment of two amino acid sequences is determined by using the Needle program from the EMBOSS package (emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence") and the amino acid sequence referred to in the claims (SEQ ID NO:2) is calculated as the number of exact matches in an alignment of the two sequences, divided by the length of the "invention sequence," or the length of the SEQ ID NO:2, whichever is the shortest. The result is expressed in percent identity.

An exact match occurs when the "invention sequence" and SEQ ID NO:2 have identical amino acid residues in the same positions of the overlap (in the alignment example below this is represented by "|"). The length of a sequence is the number of amino acid residues in the sequence (e.g. the length of amino acids 1-411 of SEQ ID NO:2 is 411).

In a purely hypothetical, alignment example below, the overlap is the amino acid sequence "HTWGER-NL" of Sequence 1; or the amino acid sequence "HGWGEDANL" of Sequence 2. In the example a gap is indicated by a "-".

Hypothetical alignment example:

```
Sequence 1:   ACMSHTWGER-NL
                  | ||| ||
Sequence 2:      HGWGEDANLAMNPS
```

In a particular embodiment, the percentage of identity of an amino acid sequence of a polypeptide with, or to, SEQ ID NO:2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

In the above hypothetical example, the number of exact matches is 6, the length of the shortest one of the two amino acid sequences is 12; accordingly the percentage of identity is 50%.

In particular embodiments of the phytase of the invention, the degree of identity to SEQ ID NO:2, SEQ ID NO:4 and/or SEQ ID NO:6 is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In still further particular embodiments, the degree of identity is at least 98.0%, 98.2%, 98.4%, 98.6%, 98.8%, 99.0%, 99.1%, 99.2%, 99.3%, 99.4%, 99.5%, 99.6%, 99.7%, 99.8%, or at least 99.9%. In alternative embodiments, the degree of identity is at least 70%, 71%, 72%, or at least 73%.

In still further particular embodiments, the phytase of the invention has no more than 2, 3, 4, 5, 6, 7, 8, 9, or no more than 10 modifications as compared to SEQ ID NO:2 SEQ ID NO:4 and/or SEQ ID NO:6 or any other parent phytase; no more than 11, 12, 13, 14, 15, 16, 17, 18, 19, or no more than 20 modifications as compared to SEQ ID NO:2; no more than 21, 22, 23, 24, 25, 26, 27, 28, 29, or no more than 30 modifications as compared to SEQ ID NO:2; no more than 31, 32, 33, 34, 35, 36, 37, 38, 39, or not more than 40 modifications as compared to SEQ ID NO:2, SEQ ID NO:4 and/or SEQ ID NO:6 or any other parent phytase; no more than 41, 42, 43, 44, 45, 46, 47, 48, 49, or no more than 50 modifications as compared to SEQ ID NO:2, SEQ ID NO:4 and/or SEQ ID NO:6 or any other parent phytase; no more than 51, 52, 53, 54, 55, 56, 57, 58, 59, or no more than 60 modifications as compared to SEQ ID NO:2, SEQ ID NO:4 and/or SEQ ID NO:6 or any other parent phytase; no more than 61, 62, 63, 64, 65, 66, 67, 68, 69, or no more than 70 modifications as compared to SEQ ID NO:2, SEQ ID NO:4 and/or SEQ ID NO:6 or any other parent phytase; no more than 71, 72, 73, 74, 75, 76, 77, 78, 79, or no more than 80 modifications as compared to SEQ ID NO:2, SEQ ID NO:4 and/or SEQ ID NO:6 or any other parent phytase; no more than 81, 82, 83, 84, 85, 86, 87, 88, 89, or no more than 90 modifications as compared to SEQ ID NO:2, SEQ ID NO:4 and/or SEQ ID NO:6 or any other parent phytase; no more than 91, 92, 93, 94, 95, 96, 97, 98, 99, or no more than 100 modifications as compared to SEQ ID NO:2, SEQ ID NO:4 and/or SEQ ID NO:6 or any other parent phytase; no more than 101, 102, 103, 104, 105, 106, 107, 108, 109, or no more than 110 modifications as compared to SEQ ID NO:2, SEQ ID NO:4 and/or SEQ ID NO:6 or any other parent phytase; no more than 111, 112, 113, 114, 115, 116, 117, 118, 119, or no more than 120 modifications as compared to SEQ ID NO:2, SEQ ID NO:4 and/or SEQ ID NO:6 or any other parent phytase; or no more than 121, 122, 123, or 124 modifications as compared to SEQ ID NO:2, SEQ ID NO:4 and/or SEQ ID NO:6 or any other parent phytase.

Position Numbering

The nomenclature used herein for defining amino acid positions is based on the amino acid sequence of the mature phytase of *Buttiauxella gaviniae* DSM 18930 which is given in the sequence listing as SEQ ID NO:2 (amino acids 1-413 of SEQ ID NO:2). Accordingly, in the present context, the basis for numbering positions is SEQ ID NO:2 starting with N1 and ending with Q413. (SEQ ID NO:2) as the standard for position numbering and, thereby, also for the nomenclature.

When used herein the term "mature" part (or sequence) refers to that part of the polypeptide which is secreted by a cell which contains, as part of its genetic equipment, a polynucleotide encoding the polypeptide. In other words, the mature polypeptide part refers to that part of the polypeptide which remains after the signal peptide part, as well as a propeptide part, if any, has been cleaved off. The signal peptide part can be predicted by programs known in the art (e.g. SignalP). Generally, the first amino acid of the mature part of an enzyme can be determined by N-terminal sequencing of the purified enzyme. Any difference between the signal peptide part and the mature part must then be due to the presence of a propeptide.

Modifications, such as Substitutions, Deletions, Insertions

A phytase variant can comprise various types of modifications relative to a template (i.e. a reference or comparative amino acid sequence such as SEQ ID NO:2): An amino acid can be substituted with another amino acid; an amino acid can be deleted; an amino acid can be inserted; as well as any combination of any number of such modifications. In the present context the term "insertion" is intended to cover also N- and/or C-terminal extensions.

The general nomenclature used herein for a single modification is the following: XDcY, where "X" and "Y" independently designate a one-letter amino acid code, or a "*" (deletion of an amino acid), "D" designates a number, and "c" designates an alphabetical counter (a, b, c, and so forth), which is only present in insertions. Reference is made to Table 1 below which describes purely hypothetical examples of applying this nomenclature to various types of modifications.

TABLE 1

| Type | Description | Example |
|---|---|---|
| Substitution | X = Amino acid in template<br>D = Position in template<br>c empty<br>Y = Amino acid in variant | G80A<br>80<br>AALNNSIGVLGVAPSAELYAVKVLGASGSG<br>\|\|\|\|\|\|\|\|:\|\|\|\|\|\|\|\|\|\|\|\|\|\|\|\|\|\|\|\|\|\|<br>AALNNSIAVLGVAPSAELYAVKVLGASGSG |
| Insertion | X = "*"<br>D = Position in template before the insertion<br>c = "a" for first insertion at this position, "b" for next, etc | *80aT *80bY *85aS<br>80     85<br>AALNNSIG..VLGVA.PSAELYAVKVLGASG<br>\|\|\|\|\|\|\|\|  \|\|\|\|\| \|\|\|\|\|\|\|\|\|\|\|\|\|\|\|\|<br>AALNNSIGTYVLGVASPSAELYAVKVLGASG |
| Deletion | X = Amino acid in template<br>D = Position in template<br>c empty<br>Y = "*" | V81*<br>80<br>AALNNSIGVLGVAPSAELYAVKVLGASGSG<br>\|\|\|\|\|\|\|\| \|\|\|\|\|\|\|\|\|\|\|\|\|\|\|\|\|\|\|\|\|\|<br>AALNNSIG.LGVAPSAELYAVKVLGASGSG |
| N-terminal extension | Insertions at position "0". | *0aA *0bT *0cG<br>1<br>...AQSVPWGISRVQ<br>\|\|\|\|\|\|\|\|\|\|\|\|<br>ATGAQSVPWGISRVQ |
| C-terminal extension | Insertions after the N-terminal amino acid. | *275aS *275bT<br>270  275<br>ATSLGSTNLYGSGLVNAEAATR..<br>\|\|\|\|\|\|\|\|\|\|\|\|\|\|\|\|\|\|\|\|\|\|\|\|<br>ATSLGSTNLYGSGLVNAEAATRST |

As explained above, the position number ("D") is counted from the first amino acid residue of SEQ ID NO:2.

Several modifications in the same sequence are separated by "/" (slash), e.g. the designation "1*/2*/3*" means that the amino acids in position number 1, 2, and 3 are all deleted, and the designation "104A/105F" means that the amino acid in position number 104 is substituted by A, and the amino acid in position number 105 is substituted by F.

Alternative modifications are separated by "," (comma), e.g., the designation "119R,K" means that the amino acid in position 119 is substituted with R or K.

The commas used herein in various other enumerations of possibilities mean what they usually do grammatically, viz. often and/or. E.g., the first comma in the listing "53V,Q, 121D, and/or 167Q" denotes an alternative (V or Q), whereas the two next commas should be interpreted as and/or options: 53 V or Q, and/or 121D, and/or 167Q.

In the present context, "at least one" (e.g. modification) means one or more, e.g. 1, 2, 3, 4, 5, 6, 7, 8, 9, or 10 modifications; or 12, 14, 15, 16, 18, 20, 22, 24, 25, 28, or 30 modifications; and so on, up to a maximum number of modifications of 125, 130, 140, 150, 160, 170, 180, 190, or of 200. The phytase variants of the invention, however, still have to be at least 70% identical to SEQ ID NO:2, this percentage being determined as described above.

A substitution or extension without any indication of what to substitute or extend with refers to the insertion of any natural, or non-natural, amino acid, except the one that occupies this position in the template.

Identifying Corresponding Position Numbers

As explained above, the mature the amino acid sequence of the mature phytase of *Buttiauxella gaviniae* DSM 18930 (SEQ ID NO:2) is used as the standard for position numbering and, thereby, also for the nomenclature.

For another phytase, in particular a phytase variant of the invention, the position corresponding to position D in SEQ ID NO:2 is found by aligning the two sequences as specified above in the section entitled "Phytase polypeptides, percentage of identity". From the alignment, the position in the sequence of the invention corresponding to position D of SEQ ID NO:2 can be clearly and unambiguously identified (the two positions on top of each other in the alignment).

Below some additional, purely hypothetical, examples are included which are derived from Table 1 above which in the third column includes a number of alignments of two sequences:

Consider the third cell in the first row of Table 1: The upper sequence is the template, the lower the variant. Position number 80 refers to amino acid residue G in the template. Amino acid A occupies the corresponding position in the variant. Accordingly, this substitution is designated G80A.

Consider now the third cell in the second row of Table 1: The upper sequence is again the template and the lower the variant. Position number 80 again refers to amino acid residue G in the template. The variant has two insertions, viz. TY, after G80 and before V81 in the template. Whereas the T and Y of course would have their own "real" position number in the variant amino acid sequence, for the present purposes we always refer to the template position numbers, and accordingly the T and the Y are said to be in position number 80a and 80b, respectively.

Finally, consider the third cell in the last row of Table 1: Position number 275 refers to the last amino acid of the template. A C-terminal extension of ST are said to be in position number 275a and 275b, respectively, although, again, of course they have their own "real" position number in the variant amino acid sequence.

Modified Properties, Reference Phytase

In a particular embodiment, the phytase of the invention has modified, preferably improved, properties. The terms "modified" and "improved" imply a comparison with another phytase. Examples of such other, reference, or comparative, phytases are: SEQ ID NO:4, and/or SEQ ID NO:6. Still further examples of reference phytases may be the GENESEQP sequences: AEH25051, AEH25056, AEH25057, AEH25058, AEH25059, AEH25060, AEH25061, AEH25062, AEH25063, AEH25064; AEH25065, AEH25066, AEH25067, AEH25068, AEH25069, AEH25070, AEH25071, AEH25072, AEH25073, AEH25074, AEH25075, or AEH25076 disclosed in FIG. 1.

Non-limiting examples of properties that are modified, preferably improved, are the following: Thermostability, pH profile, specific activity, performance in animal feed, pelleting stability, protease-sensitivity, and/or glycosylation pattern. The phytase variants produced by the method of the invention exhibits improved thermostability and may also have a modified, preferably improved, temperature profile, and/or it may incorporate a change of a potential protease cleavage site.

Thermal Performance

Thermostability

Thermostability may be determined as described in Example 3, i.e. using DSC measurements to determine the denaturation temperature, Td, of the purified phytase protein. The Td is indicative of the thermostability of the protein: The higher the Td, the higher the thermostability. Accordingly, in a preferred embodiment, the phytase of the invention has a Td which is higher than the Td of a reference phytase, wherein Td is determined on purified phytase samples (preferably with a purity of at least 90% or 95%, determined by SDS-PAGE).

Thermostability may also be determined as follows. Accordingly, in a preferred embodiment the phytase of the invention, after incubation for 60 minutes at 70° C. and pH 4.0, has an improved residual activity as compared to the residual activity of a reference phytase treated in the same way, the residual activity being calculated for each phytase relative to the activity found before the incubation (at 0 minutes). The residual activity is preferably measured on sodium phytate at pH 5.5 and 37° C. The incubation is preferably in 0.1 M sodium acetate, pH 4.0. The phytase is preferably purified, more preferably to a purity of at least 95%, determined by SDS-PAGE. A preferred phytase activity assay buffer is 0.25 M Na-acetate pH 5.5. Using this method, the residual activity of the phytase of the invention is preferably at least 105% of the residual activity of the reference phytase, more preferably at least 110%, 115%, 120%, 130%, 140%, 150%, 160%, 170%, 180%, 190%, or at least 200%. In the alternative, the residual activity relative to the activity at 0 minutes is preferably at least 31%, or at least 32%. The following substitutions providing improved thermostability stability are preferred (see Table 9): 273L, 46E, 362R, and/or 53V.

In a particular embodiment, the phytase variant of the invention is more thermostable than the reference phytase, wherein thermostability is determined using any of the above-mentioned four tests (based on the Examples).

Heat-Stability

Heat stability may be determined as described in Example 4 by determining the temperature/activity profile of the variant phytases.

Temperature Profile/Temperature Stability

Whether or not a phytase of the invention has a modified temperature profile as compared to a reference phytase may be determined as described in Example 4. Accordingly, in a particular embodiment the phytase of the invention has a modified temperature profile as compared to a reference phytase, wherein the temperature profile is determined as phytase activity as a function of temperature on sodium phytate at pH 5.5 in the temperature range of 20-90° C. (in 10° C. steps). A preferred buffer is in 0.25 M Na-acetate buffer pH 5.5. The activity at each temperature is preferably indicated as relative activity (in %) normalized to the value at optimum temperature. The optimum temperature is that temperature within the tested temperatures (i.e. those with 5-10° C. jumps) where the activity is highest.

pH Profile

Whether or not a phytase of the invention has an modified pH profile as compared to a reference phytase may be determined as described in the Examples. Accordingly, in a particular embodiment the phytase of the invention has an modified pH profile as compared to a reference phytase, wherein the pH profile is determined as phytase activity as a function of pH on sodium phytate at 37° C. in the pH range of 2.0 to 7.5 (in 0.5 pH-unit steps). A preferred buffer is a cocktail of 50 mM glycine, 50 mM acetic acid and 50 mM Bis-Tris. Another preferred buffer is 0.25M sodium acetate. The activity at each pH is preferably indicated as relative activity (in %) normalized to the value at optimum pH.

An example of an modified pH profile is where the pH curve (relative activity as a function of pH) is shifted towards higher, or lower, pH.

Another example of an modified pH profile is where the optimum pH is changed, in the upward or the downward direction A modified pH profile may also be determined by comparing phosphatase activity at pH 3.5 and 5.5. Alternatively, the activity at pH 3.5 may be compared with the activity at pH 4.0, 4.5, or 5.0. In a still further alternative embodiment, phytase activities are compared instead of phosphatase activities.

In a particular embodiment, the phytase of the invention has an modified pH profile as compared to a reference phytase. More in particular, the pH profile is modified in the pH-range of 3.5-5.5. Still more in particular, the activity at pH 4.0, 4.5, 5.0, and/or 5.5 is at a level of at least 50%, 55%, 60%, 65%, 70%, 75%, 80%, 85%, 90%, or at least 95% of the activity at the pH-optimum.

Specific Activity

In a particular embodiment, the phytase of the invention has an improved specific activity relative to a reference phytase. More in particular, the specific activity of a phytase of the invention is at least 105%, relative to the specific activity of a reference phytase determined by the same procedure. In still further particular embodiments, the relative specific activity is at least 110, 115, 120, 125, 130, 140, 145, 150, 160, 170, 180, 190, 200, 220, 240, 260, 280, 300, 350 or even 400%, still relative to the specific activity of the reference phytase as determined by the same procedure.

In the alternative, the term high specific activity refers to a specific activity of at least 200 FYT/mg Enzyme Protein (EP). In particular embodiments, the specific activity is at least 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 FYT/mg EP.

Specific activity is measured on highly purified samples (an SDS poly acryl amide gel should show the presence of only one component). The enzyme protein concentration may be determined by amino acid analysis, and the phytase activity in the units of FYT, determined as described in the Examples. Specific activity is a characteristic of the specific phytase variant in question, and it is calculated as the phytase activity measured in FYT units per mg phytase variant enzyme protein.

Performance in Animal Feed

In a particular embodiment the phytase of the invention has an improved performance in animal feed as compared to a reference phytase. The performance in animal feed may be determined by an in vitro model of Example 5. Accordingly, in a preferred embodiment the phytase of the invention has an improved performance in animal feed, wherein the performance is determined in an in vitro model, by preparing feed samples composed of 30% soybean meal and 70% maize meal with added $CaCl_2$ to a concentration of 5 g calcium per kg feed; pre-incubating them at 40° C. and pH 3.0 for 30 minutes followed by addition of pepsin (3000 U/g feed) and phytase; incubating the samples at 40° C. and pH 3.0 for 60 minutes followed by pH 4.0 for 30 minutes; stopping the reactions; extracting phytic acid and inositol-phosphates by addition of HCl to a final concentration of 0.5M and incubation at 40° C. for 2 hours, followed by one freeze-thaw cycle and 1 hour incubation at 40° C.; separating phytic acid and inositol-phosphates by high performance ion chromatography; determining the amount of residual phytate phosphorus (IP6-P); calculating the difference in residual IP6-P between the phytase-treated and a non-phytase-treated blank sample (this difference is degraded IP6-P); and expressing the degraded IP6-P of the phytase of the invention relative to degraded IP6-P of the reference phytase (e.g. the phytases having SEQ ID NO:3 and 4).

The phytase of the invention and the reference phytase are of course dosed in the same amount, preferably based on phytase activity units (FYT). A preferred dosage is 125 FYT/kg feed. Another preferred dosage is 250 FYT/kg feed. The phytases may be dosed in the form of purified phytases, or in the form of fermentation supernatants. Purified phytases preferably have a purity of at least 95%, as determined by SDS-PAGE.

In preferred embodiments, the degraded IP6-P value of the purified phytase of the invention, relative to the degraded IP6-P value of the reference phytase, is at least 101%, or at least 102%, 103%, 104%, 105%, 110%, 115%, or at least 120%. In still further preferred embodiments, the degraded IP6-P value of the purified phytase of the invention, relative to the degraded IP6-P value of the reference phytase, is at least 125%, 130%, 140%, 150%, 160%, 170%, 180%, 190%, or at least 200%. Preferably, the degraded IP6-P value of the phytase of the invention, relative to the degraded IP6-P value of the SEQ ID NO:2 phytase, is at least 105%, 110%, 113%, 115%, 120%, 125%, or at least 130%.

The relative performance of a phytase of the invention may also be calculated as the percentage of the phosphorous released by the reference phytase.

In a still further particular embodiment, the relative performance of the phytase of the invention may be calculated as the percentage of the phosphorous released by the phytase of the invention, relative to the amount of phosphorous released by the reference phytase.

In still further particular embodiments, the relative performance of the phytase of the invention is at least 105%, preferably at least 110, 120, 130, 140, 150, 160, 170, 180, 190, or at least 200%.

Nucleic Acid Sequences and Constructs

The present invention also relates to nucleic acid sequences comprising a nucleic acid sequence which encodes a phytase variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template phytase coding sequence or a subsequence thereof, wherein the mutant nucleic acid sequence encodes a variant phytase. The introduction of a mutation into the nucleic acid sequence to exchange one nucleotide for another nucleotide may be accomplished by any of the methods known in the art, e.g. by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the phytase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent phytase in question. This may, e.g., be advantageous when certain regions of the enzyme have been identified to be of particular importance for a given property of the enzyme.

Alternative methods for providing variants of the invention include gene shuffling e.g. as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence Expression Vector The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a phytase variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a phytase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The phytase variant may also be co-expressed together with at least one other enzyme of animal feed interest, such as a phytase, phosphatase, xylanase, galactanase, alpha-galactosidase, protease, phospholipase, amylase, and/or beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The phytase variant may also be expressed as a fusion protein, i.e. that the gene encoding the phytase variant has been fused in frame to the gene encoding another protein. This protein may be another enzyme or a functional domain from another enzyme.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (*Blastomycetes*). Since the classification of yeast may change in the future, for the purposes of this invention, yeast shall be defined as described in Biology and Activities of Yeast (Skinner, F. A., Passmore, S. M., and Davenport, R.R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Pichia pastoris*, *Pichia methanolica*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a phytase of the present invention comprising (a) cultivating a host cell under conditions conducive for production of the phytase; and (b) recovering the phytase.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, triticale (stabilized hybrid of wheat (*Triticum*) and rye (*Secale*), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689.; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or modifications in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e. the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may e.g. include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

The phytase of the invention may also be combined with other phytases, for example ascomycete phytases such as *Aspergillus* phytases, for example derived from *Aspergillus ficuum, Aspergillus niger*, or *Aspergillus awamori*; or basidiomycete phytases, for example derived from *Peniophora lycii, Agrocybe pediades, Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e. in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Methods for Producing Fermentation Products

Yet another aspect of the present invention relates to the methods for producing a fermentation product, such as, e.g., ethanol, beer, wine, distillers dried grains (DDG), wherein the fermentation is carried out in the presence of a phytase produced by the present invention. Examples of fermentation processes include, for example, the processes described in WO 01/62947. Fermentation is carried out using a fermenting microorganism, such as, yeast.

In a particular embodiment, the present invention provides methods for producing fermentation product, comprising (a) fermenting (using a fermenting microorganism, such as yeast) a carbohydrate containing material (e.g., starch) in the presence of a phytase of the present invention and (b) producing the fermentation product from the fermented carbohydrate containing material.

In a particular embodiment, the present invention provides methods for producing ethanol, comprising fermenting (using a fermenting microorganism, such as yeast) a carbohydrate containing material (e.g., starch) in the presence of a phytase of the present invention and producing or recovering ethanol from the fermented carbohydrate containing material.

In another embodiment, the present invention provides methods for producing ethanol comprising a) hydrolyzing starch, e.g., by a liquefaction and/or saccharification process, a raw starch hydrolysis process, b) fermenting the resulting starch in the presence of a phytase of the present invention, and c) producing ethanol.

The phytase may be added to the fermentation process at any suitable stage and in any suitable composition, including alone or in combination with other enzymes, such as, one or more alpha-amylases, glucoamylases, proteases, and/or cellulases.

In another embodiment, the present invention provides methods for producing ethanol comprising hydrolyzing biomass, and fermenting (using a fermenting microorganism, such as yeast) the resulting biomass in the presence of a phytase of the present invention.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Chemicals used are commercial products of at least reagent grade.

Example 1

Preparation of Variants, and Determination of Activity

Preparation of Phytase Variants

Expression of phytase variants in *Aspergillus oryzae*

The constructs comprising the *Buttiauxella* phytase variant genes are used to construct expression vectors for *Aspergillus*. The *Aspergillus* expression vectors may consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). The *Aspergillus* selective marker pyrG from *Aspergillus nidulans* enabling growth on miminal media for an *aspergillus* which is pyrG minus may also be present on the plasmid. The expression plasmids for phytase variants are transformed into *Aspergillus* as described in Lassen et al. (2001), Applied and Environmental Micorbiology, 67, 4701-4707. For each of the constructs 4-6 strains should be isolated, purified and cultivated in microtiterplates. Expression is determined using a p-nitrophenyl phosphate substrate. The best producing strain may be fermented in Shake flasks.

Purification of *Buttiauxella* phytase variants

The fermentation supernatant with the phytase variant is filtered through a Fast PES Bottle top filter with a 0.22 μm cut-off. The resulting solution is diluted with water to the double volume and pH was adjusted to 4.5 with acetic acid. Occasionally, the solution may become a little cloudy and this is removed by filtration through a Fast PES Bottle top filter with a 0.22 μm cut-off.

After pretreatment the phytase variant is purified by chromatography on S Sepharose, approximately 30 ml in a XK26 column, using as buffer A 50 mM sodium acetate pH 4.5, and as buffer B 50 mM sodium acetate+1 M NaCl pH 4.5. The fractions from the column are analyzed for activity using the phosphatase assay (see below) and fractions with activity are pooled.

In some cases the solution containing the purified phytase variant is concentrated using an Amicon ultra-15 filtering device with a 30 kDa cut-off membrane.

Determination of Phosphatase Activity 75 microliter phytase-containing enzyme solution is dispensed in a microtiter plate well, e.g. NUNC 269620 and 75 microliter substrate is added (for preparing the substrate, two 5 mg p-nitrophenyl phosphate tablets (Sigma, Cat. No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer. One phosphatase unit is defined as the enzyme activity that releases 1 micromol phosphate/min under the given reaction conditions (buffer blind subtracted). The absorbance of 1 micromol p-nitrophenol is determined to be 56 AU (AU=absorbancy units) under assay conditions.

Determination of Phytase Activity 75 microliter phytase-containing enzyme solution, appropriately diluted in 0.25M sodium acetate, 0.005% (w/v) Tween-20. pH5.5, is dispensed in a microtiter plate well, e.g. NUNC 269620, and 75 microliter substrate is added (prepared by dissolving 100 mg sodium phytate from rice (Aldrich Cat. No. 274321) in 10 ml 0.25M sodium acetate buffer, pH5.5). The plate is sealed and incubated 15 min. shaken with 750 rpm at 37° C. After incubation, 75 microliter stop reagent is added (the stop reagent being prepared by mixing 10 ml molybdate solution (10% (w/v) ammonium hepta-molybdate in 0.25% (w/v) ammonia solution), 10 ml ammonium vanadate (0.24% commercial product from Bie&Berntsen, Cat. No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic ortho-phosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes NS, Krogshoejvej 36, DK-2880 Bagsvaerd).

Example 2

Specific Activity

The specific activity of a phytase variant is determined on highly purified samples dialysed against 250 mM sodium acetate, pH 5.5. The purity is checked beforehand on an SDS poly acryl amide gel showing the presence of only one component.

The protein concentration is determined by amino acid analysis as follows: An aliquot of the sample is hydrolyzed in 6N HCl, 0.1% phenol for 16 h at 110° C. in an evacuated glass tube. The resulting amino acids are quantified using an Applied Biosystems 420A amino acid analysis system operated according to the manufacturer's instructions. From the amounts of the amino acids the total mass—and thus also the concentration—of protein in the hydrolyzed aliquot can be calculated.

The phytase activity is determined in the units of FYT as described in Example 1 ("Determination of phytase activity"), and the specific activity is calculated as the phytase activity measured in FYT units per mg phytase variant enzyme protein.

Example 3

Thermostability by DSC

The thermostability of the *Buttiauxella* phytase (GENESEQP accession number AEH25051) and the E54C/A101C/Q143C/I201C variant, both purified as described in Example 1, was determined by Differential Scanning calorimetry (DSC) using a VP-capillary DSC instrument (MicroCal Inc., Piscataway, N.J., USA) equipped with an auto sampler. The thermal denaturation temperature, Td (° C.), was taken as the top of denaturation peak (major endothermic peak) in thermograms (Cp vs. T) obtained after heating the phytase solutions in 50 mM sodium acetate pH 5.0 and 100 ppm Triton X at a constant programmed heating rate.

Sample and reference solutions (approx. 0.5 ml) were thermally pre-equilibrated for 10 minutes at 20° C. and the DSC scan was performed from 20 to 80° C. at a scan rate of 200 K/hour. Data-handling is performed using the MicroCal Origin software (version 7.0383). Denaturation temperatures were determined at an accuracy of approximately +/−0.5° C.

TABLE 2

Comparative Thermostability of *Buttiauxella* Phytases

| Phytase | Td (° C.) |
|---|---|
| AEH25051 | 56.5 |
| E54C/A101C/Q143C/I201C = A/C | 63.1 |

The DSC experiments shows that the E54C/A101C/Q143C/I201C variant has a significant increased thermostability compared to the reference *Buttiauxella* phytase (AEH25051).

Example 4

Temperature Profile

The temperature profile (phytase activity as a function of temperature) was determined for the *Buttiauxella* phytase (GENESEQP accession number AEH25051) and variants in the temperature range of 20-80° C. essentially as described above ("Determination of phytase activity"). However, the enzymatic reactions (100 microliter phytase-containing enzyme solution +100 microliter substrate) were performed in PCR tubes instead of microtiter plates. After a 15 minute reaction period at desired temperature the tubes were cooled to 10° C. for 30 seconds and 150 microliter of each reaction mixture was transferred to a microtiter plate. 75 microliter stop reagent was added and the absorbance at 405 nm was measured in a microtiter plate spectrophotometer. The results are summarized in Table 3. The numbers given for each temperature are relative activity (in %) normalized to the value at optimum.

TABLE 3

Relative temperature profiles

| Phytase variant | Temperature (° C.) | | | | | | | | | | | |
|---|---|---|---|---|---|---|---|---|---|---|---|---|
| | 20 | 30 | 40 | 50 | 55 | 60 | 63 | 65 | 67 | 70 | 75 | 80 |
| AEH25051 | 27 | 43 | 64 | 84 | 100 | 98 | 68 | 26 | 14 | 9 | 7 | 7 |
| D33C/E54C/A101C/W179C = B/C | 26 | 44 | 66 | 88 | 98 | 100 | 92 | 66 | 38 | 10 | 7 | 5 |
| E54C/A101C/Q143C/I201C = A/C | 26 | 45 | 66 | 87 | 100 | 96 | 79 | 52 | 32 | 10 | 7 | 6 |

For both variants the temperature profiles are shifted to higher temperature compared to the temperature profile of the reference *Buttiauxella* phytase (AEH25051).

Example 5

Performance in Animal Feed in an In Vitro Model

The performance in animal feed of a number of phytase variants of the invention is compared in an in vitro model to the performance of a reference protein such as SEQ ID NO:2. The in vitro model simulates gastro-intestinal conditions in a monogastric animal and correlates well with results obtained in animal trials in vivo. The version used in this example simulates the crop and stomach of a broiler. The comparison is performed as follows:

Phytase activity in the variant sample is determined as described in Example 1 under "Determination of phytase activity".

Feed pellets from a broiler feeding trial—and with maize, soybean meal and soybean oil as main constituents—are pre-incubated at 40° C. and pH 4.6 for 5 minutes followed by the addition of suitable dosages of the phytases (identical dosages are used for all phytases to be tested to allow comparison), for example between 125 to 1000 phytase units FYT/kg feed, or buffer in the control samples. After 5 minutes of incubation, pepsin (3000 U/g feed) in an HCl-solution is added and in this way pH is reduced to 3. The samples are then incubated at 40° C. for another 5 minutes.

The reactions are stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates are separated by high performance ion chroma-tography as described by Chen et al in Journal of Chromatography A (2003) vol. 1018, pp. 41-52 and quantified as described by Skoglund et al in J. Agric. Food Chem. (1997), vol. 45, pp. 431-436.

Degradation of phytate is then calculated as the difference in inositol-6-phosphate bound phosphorous (IP6-P) between phytase-treated and non-treated samples. The relative performance of the variant is calculated as the percentage of phytate degradation by the wild type phytase.

Example 6

Performance in an In Vivo Pig Trial

Comparative evaluation of the effects of graded amounts of the *Buttiauxella* wild type phytase and a variant on the faecal digestibility and excretion of phosphorus and calcium in growing pigs.

Sixty four Large White×Landrace pigs having an initial body weight of 43.55±4.35 kg are used.

The animals are housed in floor-pen cages in an environmentally controlled room. Each pen has a plastic-coated welded wire floor and is equipped with two water nipples and four stainless-steel individualized feeders. Room temperature was 21-22° C. and humidity percentage is 50%.

The pigs are fed a basal diet formulated to provide phosphorus (P) exclusively from vegetable origin during an adaptive period of 14 days. After that period they are allocated into 16 equal groups of 4 animals each.

They are fed for 12 days the basal diet or this diet supplemented with 1000 or 2000 U/kg of *Buttiauxella* wild type phytase or with 500, 1000 or 2000 U/kg of the variant designated 100 having 2 additional disulfide bonds.

An indigestible tracer (chromium oxide) is added at a concentration of 0.4% to all the diets allowing calculation of the digestibility of P and calcium (Ca). The feed is distributed ad libitum in mash form, under pen feed consumption control, and the animals has free access to drinking water. The digestibility of Ca is not corrected for Ca intake with the drinking water. Faecal P, Ca and Cr concentrations are measured at the $12^{th}$ day of the second period. Faeces were sampled individually, in approximately the same amount at the same time of the day, during the last 3 days preceding that date. Thus, for each dietary treatment and for each criterion a total of 12 individual determinations are performed. All minerals are determined according to standard Association of Official Analytical Chemists (1990) methods using a Vista-MPX ICP-OES spectrometer. The apparent digestibility (% of the intake) of the minerals is calculated for the mentioned 3 day period.

---

The invention claimed is:

1. A variant phytase which
   a) has at least 80% identity to amino acids 1-413 of SEQ ID NO:2, amino acids 1-413 of SEQ ID NO:4, and/or amino acids 1-413 of SEQ ID NO:6 when aligned to the respective amino acid sequence using the Needle program with the BLOSUM62 substitution matrix, a gap opening penalty of 10.0, and a gap extension penalty of 0.5; and
   b) comprises a disulfide bridge at one or more position pairs selected from the group consisting of: A) 143C/201c, B) 33C/179C, C) 54C/101C, D) 93C/48C, E) 33C/178C, F) 61C/102C, and G) 164C/251C.

2. The variant phytase of claim 1, which comprises a disulfide bridge at the position pair A) 143C/201C.

3. The variant phytase of claim 1, which comprises a disulfide bridge at the position pair B) 33C/179C.

4. The variant phytase of claim 1, which comprises a disulfide bridge at the position pair C) 54C/101C.

5. The variant phytase of claim 1, which comprises a disulfide bridge at the position pair D) 93C/48C.

6. The variant phytase of claim 1, which comprises a disulfide bridge at the position pair E) 33C/178C.

7. The variant phytase of claim 1, which comprises a disulfide bridge at the position pair F) 61C/102C.

8. The variant phytase of claim 1, which comprises a disulfide bridge at the position pair G) 164C/251C.

9. The variant phytase of claim 1, which comprises a disulfide bridge at the position pairs A) 143C/201C and C) 54C/101C.

10. The variant phytase of claim 1, which comprises a disulfide bridge at the position pairs B) 33C/179C and C) 54C/101C.

11. The variant phytase of claim 1, which has at least 85% identity to amino acids 1-413 of SEQ ID NO:2, amino acids 1-413 of SEQ ID NO:4, and/or amino acids 1-413 of SEQ ID NO:6.

12. The variant phytase of claim 1, which has at least 90% identity to amino acids 1-413 of SEQ ID NO:2, amino acids 1-413 of SEQ ID NO:4, and/or amino acids 1-413 of SEQ ID NO:6.

13. The variant phytase of claim 1, which has at least 95% identity to amino acids 1-413 of SEQ ID NO:2, amino acids 1-413 of SEQ ID NO:4, and/or amino acids 1-413 of SEQ ID NO:6.

14. The variant phytase of claim 1, which comprises a disulfide bridge at the two position pairs:
A+B, A+D, A+E, A+F, A+G, B+D, B+E, B+F, B+G, C+D, C+E, C+F, C+G, D+E, D+F, D+G, E+F, E+G, or F+G, wherein A means 143C/201C, B means 33C/179C, C means 54C/101C, D means 93C/48C, E means 33C/178C, F means 61C/102C, and G means 164C/251 C.

15. The variant phytase of claim 1, which comprises a disulfide bridge at the three position pairs:
A+B+C, A+B+D, A+B+E, A+B+F, A+B+G, A+C+D, A+C+E, A+C+F, A+C+G, A+D+E, A+D+F, A+D+G, A+E+F, A+E+G, A+F+G, B+C+D, B+C+E, B+C+F, B+C+G, B+D+E, B+D+F, B+D+G, B+E+F, B+E+G, B+F+G, C+D+E, C+D+F, C+D+G, C+E+F, C+E+G, C+F+G, D+E+F, D+E+G, D+F+G, or E+F+G, wherein A means 143C/201 C, B means 33C/179C, C means 54C/101C, D means 93C/48C, E means 33C/178C, F means 61C/102C, and G means 164C/251C.

16. The variant phytase of claim 1, which comprises a disulfide bridge at the four position pairs:
A+B+C+D, A+B+C+E, A+B+C+F, A+B+C+G, A+B+D+E, A+B+D+F, A+B+D+G, A+B+E+F, A+B+E+G, A+B+F+G, A+C+D+E, A+C+D+F, A+C+D+G, A+C+E+F, A+C+E+G, A+C+E+H, A+C+F+G, A+D+E+F, A+D+E+G, A+D+F+G, A+E+F+G, B+C+D+E, B+C+D+F, B+C+D+G, B+C+E+F, B+C+E+G, B+C+F+G, B+D+E+F, B+D+E+G, B+D+F+G, B+E+F+G, C+D+E+F, C+D+E+G, C+D+F+G, C+E+F+G, C+E+F+H, or D+E+F+G, wherein A means 143C/201C, B means 33C/179C, C means 54C/101C, D means 93C/48C, E means 33C/178C, F means 61C/102C, and G means 164C/251C.

17. The variant phytase of claim 1, which comprises a disulfide bridges at the five position pairs:
A+B+C+D+E, A+B+C+D+F, A+B+C+D+G, A+B+C+E+F, A+B+C+E+G, A+B+C+F+G, A+B+D+E+F, A+B+D+E+G, A+B+D+F+G, A+B+E+F+G, A+B+F+G+H, A+C+D+E+F, A+C+D+E+G, A+C+D+F+G, A+C+E+F+G, A+D+E+F+G, B+C+D+E+F, B+C+D+E+G, B+C+D+F+G, B+C+E+F+G, B+D+E+F+G, or C+D+E+F+G, wherein A means 143C/201C, B means 33C/179C, C means 54C/101C, D means 93C/48C, E means 33C/178C, F means 61C/102C, and G means 164C/251C.

18. The variant phytase of claim 1, which comprises a disulfide bridge at the six position pairs:
A+B+C+D+E+F, A+B+C+D+E+G, A+B+C+D+F+G, A+B+C+E+F+G, A+B+D+E+F+G, A+C+D+E+F+G, or B+C+D+E+F+G, wherein A means 143C/201C, B means 33C/179C, C means 54C/101C, D means 93C/48C, E means 33C/178C, F means 61C/102C, and G means 164C/251C.

19. The variant phytase of claim 1, which comprises a disulfide bridge at the seven position pairs:
A+B+C+D+E+F+G, wherein A means 143C/201C, B means 33C/179C, C means 54C/101C, D means 93C/48C, E means 33C/178C, F means 61C/102C, and G means 164C/251C.

20. The variant phytase of claim 1, wherein the substitutions to establish the disulfide bridges are:
A'. Q143C/I201C
B'. D33C/W179C
C'. E54C/A101C
D'. Q93C/Y48C
E'. D33C/A178C
F'. G61C/F102C
G'. F164C/K251C.

21. The variant phytase of claim 1, which is a variant of the mature phytase of SEQ ID NO:2, SEQ ID NO:4, or SEQ ID NO:6, or any one of the following sequences: AEH25051 (SEQ ID NO: 7), AEH25056 (SEQ ID NO: 8), AEH25057 (SEQ ID NO: 9), AEH25058 (SEQ ID NO: 10), AEH25059 (SEQ ID NO: 11), AEH25060 (SEQ ID NO: 12), AEH25061 (SEQ ID NO: 13), AEH25062 (SEQ ID NO: 14), AEH25063 (SEQ ID NO: 15), AEH25064 (SEQ ID NO: 16), AEH25065 (SEQ ID NO: 17), AEH25066 (SEQ ID NO: 18), AEH25067 (SEQ ID NO: 19), AEH25068 (SEQ ID NO: 20), AEH25069 (SEQ ID NO: 21), AEH25070 (SEQ ID NO: 22), AEH25071 (SEQ ID NO: 23), AEH25072 (SEQ ID NO: 24), AEH25073 (SEQ ID NO: 25), AEH25074 (SEQ ID NO: 26), AEH25075 (SEQ ID NO: 27), or AEH25076 (SEQ ID NO: 28).

22. A composition comprising at least one phytase variant of claim 1, and
(a) at least one fat soluble vitamin;
(b) at least one water soluble vitamin; and/or
(c) at least one trace mineral.

23. An animal feed composition having a crude protein content of 50 to 800 g/kg and comprising the phytase variant of claim 1.

24. A method for improving the nutritional value of an animal feed, comprising adding the phytase variant of claim 1 to the feed.

25. A process for reducing phytate levels in animal manure comprising feeding an animal with an effective amount of the feed composition of claim 22.

26. A method for the treatment of vegetable proteins, comprising the step of adding the phytase variant of claim 1 to at least one vegetable protein.

27. A method for producing a fermentation product comprising fermenting a carbohydrate material in the presence of the phytase variant of claim 1.

28. A method of producing a variant phytase of claim 1, comprising introducing a disulfide bridge at one or more position pairs selected from the group consisting of: A) 143C/201C, B) 33C/179C, C) 54C/101C, D) 93C/48C, E) 33C/178C, F) 61C/102C, and G) 164C/251C.

29. The variant phytase of claim 1, which has at least 91% identity to amino acids 1-413 of SEQ ID NO:2, amino acids 1-413 of SEQ ID NO:4, and/or amino acids 1-413 of SEQ ID NO:6.

30. The variant phytase of claim 1, which has at least 92% identity to amino acids 1-413 of SEQ ID NO:2, amino acids 1-413 of SEQ ID NO:4, and/or amino acids 1-413 of SEQ ID NO:6.

31. The variant phytase of claim 1, which has at least 93% identity to amino acids 1-413 of SEQ ID NO:2, amino acids 1-413 of SEQ ID NO:4, and/or amino acids 1-413 of SEQ ID NO:6.

32. The variant phytase of claim 1, which has at least 94% identity to amino acids 1-413 of SEQ ID NO:2, amino acids 1-413 of SEQ ID NO:4, and/or amino acids 1-413 of SEQ ID NO:6.

* * * * *

SEQUENCE LISTING

```
<160> NUMBER OF SEQ ID NOS: 29

<210> SEQ ID NO 1
<211> LENGTH: 1341
<212> TYPE: DNA
<213> ORGANISM: Buttiauxella gaviniae DSM18930
<220> FEATURE:
<221> NAME/KEY: CDS
<222> LOCATION: (1)..(1338)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1338)

<400> SEQUENCE: 1 atg acg atc tct gcg ttt aac cac aaa aaa ctg acg ctt cac cct ggt        48
Met Thr Ile Ser Ala Phe Asn His Lys Lys Leu Thr Leu His Pro Gly
            -30                 -25                 -20 ctg ttc gta gca ctg agc gcc ata ttt tca tta ggc tct acg gca tat        96
Leu Phe Val Ala Leu Ser Ala Ile Phe Ser Leu Gly Ser Thr Ala Tyr
        -15                 -10                  -5 gcc aat gac act ccc gct tca ggc tac cag gtt gaa aaa gtg gtt atc       144
Ala Asn Asp Thr Pro Ala Ser Gly Tyr Gln Val Glu Lys Val Val Ile
 -1   1               5                  10                  15 ctc agc cgc cac ggt gtg cga gcc ccc acc aaa atg aca cag act atg       192
Leu Ser Arg His Gly Val Arg Ala Pro Thr Lys Met Thr Gln Thr Met
                20                  25                  30 cgc gac gta aca ccc aat acc tgg cca gaa tgg cca gta aaa ctg ggt       240
Arg Asp Val Thr Pro Asn Thr Trp Pro Glu Trp Pro Val Lys Leu Gly
            35                  40                  45 tat atc acg cca cgc ggt gag cat ctg att agc ctg atg ggc ggg ttt       288
Tyr Ile Thr Pro Arg Gly Glu His Leu Ile Ser Leu Met Gly Gly Phe
        50                  55                  60 tat cgc gag aag ttt caa caa cag ggc att tta tcg cag ggc agt tgc       336
Tyr Arg Glu Lys Phe Gln Gln Gln Gly Ile Leu Ser Gln Gly Ser Cys
    65                  70                  75 ccc aca cca aac tca att tat gtc tgg gca gac gtt gat cag cgc acg       384
Pro Thr Pro Asn Ser Ile Tyr Val Trp Ala Asp Val Asp Gln Arg Thr
 80                  85                  90                  95 ctt aaa act ggc gaa gct ttc ctg gca ggg ctt gct ccg caa tgt ggt       432
Leu Lys Thr Gly Glu Ala Phe Leu Ala Gly Leu Ala Pro Gln Cys Gly
                100                 105                 110 tta act att cac cac caa cag aat ctt gaa aaa gcc gat ccg ctg ttc       480
Leu Thr Ile His His Gln Gln Asn Leu Glu Lys Ala Asp Pro Leu Phe
            115                 120                 125 cat ccg gtg aaa gcg ggc acc tgt tca atg gat aaa act cgg ctc caa       528
His Pro Val Lys Ala Gly Thr Cys Ser Met Asp Lys Thr Arg Leu Gln
        130                 135                 140 cag gcc gtt gaa aaa gaa gct caa acg ccc att gag aat ctg aac cag       576
Gln Ala Val Glu Lys Glu Ala Gln Thr Pro Ile Glu Asn Leu Asn Gln
    145                 150                 155
```

```
cac tat att ccc tct ctg gct ttg atg aac acg acc ctc aac ttt tcg    624
His Tyr Ile Pro Ser Leu Ala Leu Met Asn Thr Thr Leu Asn Phe Ser
160             165                 170                 175 acg tct gcc tgg tgt cag aaa cac agc gcg gat aaa agc tgt gat tta    672
Thr Ser Ala Trp Cys Gln Lys His Ser Ala Asp Lys Ser Cys Asp Leu
            180                 185                 190 gcg caa tcc atg ccg agc aag ctg tcg ata aaa gat aat ggc aac aaa    720
Ala Gln Ser Met Pro Ser Lys Leu Ser Ile Lys Asp Asn Gly Asn Lys
        195                 200                 205 gtc gct ctc gat ggg gct gtt ggt ctt tca tcc act ctt gct gaa att    768
Val Ala Leu Asp Gly Ala Val Gly Leu Ser Ser Thr Leu Ala Glu Ile
    210                 215                 220 ttc ctg ctg gaa tat gcg caa ggg atg ccg caa gcg gcc tgg ggg aag    816
Phe Leu Leu Glu Tyr Ala Gln Gly Met Pro Gln Ala Ala Trp Gly Lys
225                 230                 235 att cat tca gag caa gat tgg gcg gag ttg ctg aaa ctg cat aac gcc    864
Ile His Ser Glu Gln Asp Trp Ala Glu Leu Leu Lys Leu His Asn Ala
240                 245                 250                 255 cag ttt gat ttg atg gcg cgc aca cct tat atc gcc aga cat aac gga    912
Gln Phe Asp Leu Met Ala Arg Thr Pro Tyr Ile Ala Arg His Asn Gly
            260                 265                 270 acg cct tta ttg cag gcc atc agc aac gcg ctg gac cca aac gcc acc    960
Thr Pro Leu Leu Gln Ala Ile Ser Asn Ala Leu Asp Pro Asn Ala Thr
        275                 280                 285 gca agc aag ctg cct gat atc tcg ccg gac aat aag atc ctg ttt att    1008
Ala Ser Lys Leu Pro Asp Ile Ser Pro Asp Asn Lys Ile Leu Phe Ile
    290                 295                 300 gcc gga cac gat acc aat atc gcc aac atc tca ggc atg ctc aac atg    1056
Ala Gly His Asp Thr Asn Ile Ala Asn Ile Ser Gly Met Leu Asn Met
305                 310                 315 cgc tgg acg cta ccc gga caa cca gat aac act cct cca ggc ggc gct    1104
Arg Trp Thr Leu Pro Gly Gln Pro Asp Asn Thr Pro Pro Gly Gly Ala
320                 325                 330                 335 ttg atc ttt gaa cgc ctg gct gat aaa gct ggg aaa caa tat gtt agt    1152
Leu Ile Phe Glu Arg Leu Ala Asp Lys Ala Gly Lys Gln Tyr Val Ser
            340                 345                 350 gtg agt atg gtg tat cag aca ctc gag cag ttg cgc gct caa aca ccg    1200
Val Ser Met Val Tyr Gln Thr Leu Glu Gln Leu Arg Ala Gln Thr Pro
        355                 360                 365 ctt agc ctt aag gaa ccc gca gga agt gtg cag cta aaa att cct ggc    1248
Leu Ser Leu Lys Glu Pro Ala Gly Ser Val Gln Leu Lys Ile Pro Gly
    370                 375                 380 tgt aat gac cag acg gct gaa gga tat tgc ccg ctg cca aca ttt aaa    1296
Cys Asn Asp Gln Thr Ala Glu Gly Tyr Cys Pro Leu Pro Thr Phe Lys
385                 390                 395 cgc gtg gtt agc caa agt gaa gaa ccg ggc tgc cag cta cag taa         1341
Arg Val Val Ser Gln Ser Glu Glu Pro Gly Cys Gln Leu Gln
400                 405                 410

<210> SEQ ID NO 2
<211> LENGTH: 446
<212> TYPE: PRT
<213> ORGANISM: Buttiauxella gaviniae DSM18930

<400> SEQUENCE: 2

Met Thr Ile Ser Ala Phe Asn His Lys Lys Leu Thr Leu His Pro Gly
            -30                 -25                 -20

Leu Phe Val Ala Leu Ser Ala Ile Phe Ser Leu Gly Ser Thr Ala Tyr
        -15                 -10                 -5

Ala Asn Asp Thr Pro Ala Ser Gly Tyr Gln Val Glu Lys Val Val Ile
```

```
   -1   1                   5                    10                   15
  Leu Ser Arg His Gly Val Arg Ala Pro Thr Lys Met Thr Gln Thr Met
                          20                   25                   30

Arg Asp Val Thr Pro Asn Thr Trp Pro Glu Trp Pro Val Lys Leu Gly
                  35                   40                   45

Tyr Ile Thr Pro Arg Gly Glu His Leu Ile Ser Leu Met Gly Gly Phe
                  50                   55                   60

Tyr Arg Glu Lys Phe Gln Gln Gln Gly Ile Leu Ser Gln Gly Ser Cys
          65                   70                   75

Pro Thr Pro Asn Ser Ile Tyr Val Trp Ala Asp Val Asp Gln Arg Thr
  80                   85                   90                   95

Leu Lys Thr Gly Glu Ala Phe Leu Ala Gly Leu Ala Pro Gln Cys Gly
                      100                 105                 110

Leu Thr Ile His His Gln Gln Asn Leu Glu Lys Ala Asp Pro Leu Phe
                 115                  120                 125

His Pro Val Lys Ala Gly Thr Cys Ser Met Asp Lys Thr Arg Leu Gln
                 130                  135                 140

Gln Ala Val Glu Lys Glu Ala Gln Thr Pro Ile Glu Asn Leu Asn Gln
          145                  150                 155

His Tyr Ile Pro Ser Leu Ala Leu Met Asn Thr Thr Leu Asn Phe Ser
  160                 165                  170                 175

Thr Ser Ala Trp Cys Gln Lys His Ser Ala Asp Lys Ser Cys Asp Leu
                  180                 185                  190

Ala Gln Ser Met Pro Ser Lys Leu Ser Ile Lys Asp Asn Gly Asn Lys
                  195                 200                  205

Val Ala Leu Asp Gly Ala Val Gly Leu Ser Ser Thr Leu Ala Glu Ile
              210                  215                 220

Phe Leu Leu Glu Tyr Ala Gln Gly Met Pro Gln Ala Ala Trp Gly Lys
              225                  230                 235

Ile His Ser Glu Gln Asp Trp Ala Glu Leu Leu Lys Leu His Asn Ala
  240                 245                  250                 255

Gln Phe Asp Leu Met Ala Arg Thr Pro Tyr Ile Ala Arg His Asn Gly
                  260                 265                  270

Thr Pro Leu Leu Gln Ala Ile Ser Asn Ala Leu Asp Pro Asn Ala Thr
                  275                 280                  285

Ala Ser Lys Leu Pro Asp Ile Ser Pro Asp Asn Lys Ile Leu Phe Ile
              290                  295                 300

Ala Gly His Asp Thr Asn Ile Ala Asn Ile Ser Gly Met Leu Asn Met
  305                 310                  315

Arg Trp Thr Leu Pro Gly Gln Pro Asp Asn Thr Pro Pro Gly Gly Ala
  320                 325                  330                 335

Leu Ile Phe Glu Arg Leu Ala Asp Lys Ala Gly Lys Gln Tyr Val Ser
                  340                 345                  350

Val Ser Met Val Tyr Gln Thr Leu Glu Gln Leu Arg Ala Gln Thr Pro
              355                  360                 365

Leu Ser Leu Lys Glu Pro Ala Gly Ser Val Gln Leu Lys Ile Pro Gly
              370                  375                 380

Cys Asn Asp Gln Thr Ala Glu Gly Tyr Cys Pro Leu Pro Thr Phe Lys
  385                 390                  395

Arg Val Val Ser Gln Ser Glu Glu Pro Gly Cys Gln Leu Gln
  400                 405                  410
```

<210> SEQ ID NO 3

<211> LENGTH: 1271
<212> TYPE: DNA
<213> ORGANISM: Buttiauxella agrestis DSM18931
<220> FEATURE:
<221> NAME/KEY: CDS
<222> LOCATION: (3)..(1268)
<220> FEATURE:
<221> NAME/KEY: sig_peptide
<222> LOCATION: (3)..(29)
<220> FEATURE:
<221> NAME/KEY: mat_peptide
<222> LOCATION: (30)..(1268)

<400> SEQUENCE: 3

```
ca ttt tca tta ggt tta acg gca tat gcc agc gac act ccc gct tca         47
   Phe Ser Leu Gly Leu Thr Ala Tyr Ala Ser Asp Thr Pro Ala Ser
              -5              -1  1              5 ggc tac cag att gaa aaa gtg gta ata ctc agc cgc cac ggt gtg cga        95
Gly Tyr Gln Ile Glu Lys Val Val Ile Leu Ser Arg His Gly Val Arg
        10                  15                  20 gca ccc acc aaa atg aca cag acc atg cgc gac gta aca ccc aat tcc      143
Ala Pro Thr Lys Met Thr Gln Thr Met Arg Asp Val Thr Pro Asn Ser
    25                  30                  35 tgg ccc gaa tgg ccg gta aaa ttg ggt tat atc acg cca cgc ggt gag      191
Trp Pro Glu Trp Pro Val Lys Leu Gly Tyr Ile Thr Pro Arg Gly Glu
40                  45                  50 cat ctg att agc ctg atg ggc ggg ttt tat cgc cag aag ttt caa caa      239
His Leu Ile Ser Leu Met Gly Gly Phe Tyr Arg Gln Lys Phe Gln Gln
55                  60                  65                  70 aag ggc att tta tcg cag ggc agt tgc ccc aca cca aac tca att tat      287
Lys Gly Ile Leu Ser Gln Gly Ser Cys Pro Thr Pro Asn Ser Ile Tyr
            75                  80                  85 gtc tgg gca gac gtt gat cag cgc acg ctt aaa acg ggc gaa gct ttc      335
Val Trp Ala Asp Val Asp Gln Arg Thr Leu Lys Thr Gly Glu Ala Phe
        90                  95                 100 ctg gca ggg ctt gct ccg caa tgt ggt tta act att cac cac cag cag      383
Leu Ala Gly Leu Ala Pro Gln Cys Gly Leu Thr Ile His His Gln Gln
    105                 110                 115 aat ctt gaa aaa gcc gat ccg ctg ttc cat ccg gtg aaa gcg ggc acc      431
Asn Leu Glu Lys Ala Asp Pro Leu Phe His Pro Val Lys Ala Gly Thr
120                 125                 130 tgt tca atg gat aaa act caa gtc cag cag gcc gtt gaa aaa gaa gct      479
Cys Ser Met Asp Lys Thr Gln Val Gln Gln Ala Val Glu Lys Glu Ala
135                 140                 145                 150 caa atg ccc att gag aat ctg aac cag cac tat att ccc tct ctg gcc      527
Gln Met Pro Ile Glu Asn Leu Asn Gln His Tyr Ile Pro Ser Leu Ala
                155                 160                 165 ttg atg aac acg act ctc aac ttt tcg acg tct gcc tgg tgc cag aaa      575
Leu Met Asn Thr Thr Leu Asn Phe Ser Thr Ser Ala Trp Cys Gln Lys
            170                 175                 180 cac agc gcg gat aaa agc tgt gat tta gcg caa tcc atg ccg agc aag      623
His Ser Ala Asp Lys Ser Cys Asp Leu Ala Gln Ser Met Pro Ser Lys
        185                 190                 195 ctg tcg ata aaa gat aat ggc aac aaa gtc gct ctt gat ggg gcc att      671
Leu Ser Ile Lys Asp Asn Gly Asn Lys Val Ala Leu Asp Gly Ala Ile
    200                 205                 210 ggc ctt tcg tct acg ctt gct gaa att ttc ctg ctg gaa tat gcg caa      719
Gly Leu Ser Ser Thr Leu Ala Glu Ile Phe Leu Leu Glu Tyr Ala Gln
215                 220                 225                 230 ggg atg ccg caa gcg gcg tgg ggg aat att cat tca gag caa gag tgg      767
Gly Met Pro Gln Ala Ala Trp Gly Asn Ile His Ser Glu Gln Glu Trp
                235                 240                 245
```

|  |  |  |  |  |  |  |  |  |  |  |  |  |  |  |  |
|---|---|---|---|---|---|---|---|---|---|---|---|---|---|---|---|
| gcg | tcg | cta | ttg | aaa | ctg | cat | aac | acc | cag | ttt | gat | ttg | atg | gcg | cgc | 815 |
| Ala | Ser | Leu | Leu | Lys | Leu | His | Asn | Thr | Gln | Phe | Asp | Leu | Met | Ala | Arg |
|  |  |  | 250 |  |  |  |  | 255 |  |  |  | 260 |  |  |  |

|  |  |  |  |  |  |  |  |  |  |  |  |  |  |  |  |
|---|---|---|---|---|---|---|---|---|---|---|---|---|---|---|---|
| aca | cct | tac | atc | gcc | gca | cat | aac | gga | acg | ccg | tta | ttg | cag | acc | atc | 863 |
| Thr | Pro | Tyr | Ile | Ala | Ala | His | Asn | Gly | Thr | Pro | Leu | Leu | Gln | Thr | Ile |
|  |  | 265 |  |  |  |  | 270 |  |  |  |  | 275 |  |  |  |

|  |  |  |  |  |  |  |  |  |  |  |  |  |  |  |  |
|---|---|---|---|---|---|---|---|---|---|---|---|---|---|---|---|
| agc | aac | gcg | ctg | gag | ccg | aaa | gcc | gac | gta | agc | aaa | ctg | cct | gat | atc | 911 |
| Ser | Asn | Ala | Leu | Glu | Pro | Lys | Ala | Asp | Val | Ser | Lys | Leu | Pro | Asp | Ile |
|  | 280 |  |  |  |  | 285 |  |  |  |  | 290 |  |  |  |  |

|  |  |  |  |  |  |  |  |  |  |  |  |  |  |  |  |
|---|---|---|---|---|---|---|---|---|---|---|---|---|---|---|---|
| tca | tct | gac | aat | aag | atc | ctg | ttt | att | gcc | gga | cac | gat | acc | aat | att | 959 |
| Ser | Ser | Asp | Asn | Lys | Ile | Leu | Phe | Ile | Ala | Gly | His | Asp | Thr | Asn | Ile |
| 295 |  |  |  | 300 |  |  |  |  | 305 |  |  |  |  | 310 |  |

|  |  |  |  |  |  |  |  |  |  |  |  |  |  |  |  |
|---|---|---|---|---|---|---|---|---|---|---|---|---|---|---|---|
| gcc | aat | atc | gca | ggc | atg | ctc | aac | atg | cgc | tgg | acg | cta | cca | ggg | caa | 1007 |
| Ala | Asn | Ile | Ala | Gly | Met | Leu | Asn | Met | Arg | Trp | Thr | Leu | Pro | Gly | Gln |
|  |  |  |  | 315 |  |  |  |  | 320 |  |  |  |  | 325 |  |

|  |  |  |  |  |  |  |  |  |  |  |  |  |  |  |  |
|---|---|---|---|---|---|---|---|---|---|---|---|---|---|---|---|
| ccc | gat | aac | acc | cca | ccg | ggc | ggc | gct | tta | gtc | ttt | gag | cgt | ttg | gcc | 1055 |
| Pro | Asp | Asn | Thr | Pro | Pro | Gly | Gly | Ala | Leu | Val | Phe | Glu | Arg | Leu | Ala |
|  |  |  | 330 |  |  |  |  | 335 |  |  |  |  | 340 |  |  |

|  |  |  |  |  |  |  |  |  |  |  |  |  |  |  |  |
|---|---|---|---|---|---|---|---|---|---|---|---|---|---|---|---|
| gat | aag | tca | ggg | aaa | caa | tat | att | agc | gtg | agc | atg | gtg | tat | cag | act | 1103 |
| Asp | Lys | Ser | Gly | Lys | Gln | Tyr | Ile | Ser | Val | Ser | Met | Val | Tyr | Gln | Thr |
|  |  | 345 |  |  |  |  | 350 |  |  |  |  | 355 |  |  |  |

|  |  |  |  |  |  |  |  |  |  |  |  |  |  |  |  |
|---|---|---|---|---|---|---|---|---|---|---|---|---|---|---|---|
| ctt | gag | cag | ttg | cgc | gct | caa | aca | cca | ctt | agc | ctt | aat | gaa | cca | gcg | 1151 |
| Leu | Glu | Gln | Leu | Arg | Ala | Gln | Thr | Pro | Leu | Ser | Leu | Asn | Glu | Pro | Ala |
| 360 |  |  |  |  | 365 |  |  |  |  | 370 |  |  |  |  |  |

|  |  |  |  |  |  |  |  |  |  |  |  |  |  |  |  |
|---|---|---|---|---|---|---|---|---|---|---|---|---|---|---|---|
| ggt | agc | gta | cag | cta | aaa | att | cct | ggc | tgt | aac | gac | cag | acg | gct | gaa | 1199 |
| Gly | Ser | Val | Gln | Leu | Lys | Ile | Pro | Gly | Cys | Asn | Asp | Gln | Thr | Ala | Glu |
| 375 |  |  |  |  | 380 |  |  |  |  | 385 |  |  |  |  | 390 |

|  |  |  |  |  |  |  |  |  |  |  |  |  |  |  |  |
|---|---|---|---|---|---|---|---|---|---|---|---|---|---|---|---|
| gga | tac | tgc | cca | ctg | tcg | acg | ttc | aca | cgc | gtg | gtt | agc | caa | agc | gtg | 1247 |
| Gly | Tyr | Cys | Pro | Leu | Ser | Thr | Phe | Thr | Arg | Val | Val | Ser | Gln | Ser | Val |
|  |  |  |  | 395 |  |  |  |  | 400 |  |  |  |  | 405 |  |

|  |  |  |  |  |  |
|---|---|---|---|---|---|
| gaa | cca | ggc | tgc | cag | cta | ccg | taa | 1271 |
| Glu | Pro | Gly | Cys | Gln | Leu | Pro |
|  |  | 410 |  |  |  |  |

<210> SEQ ID NO 4
<211> LENGTH: 422
<212> TYPE: PRT
<213> ORGANISM: Buttiauxella agrestis DSM18931

<400> SEQUENCE: 4

Phe Ser Leu Gly Leu Thr Ala Tyr Ala Ser Asp Thr Pro Ala Ser Gly
                -5              -1   1               5

Tyr Gln Ile Glu Lys Val Val Ile Leu Ser Arg His Gly Val Arg Ala
            10                  15                  20

Pro Thr Lys Met Thr Gln Thr Met Arg Asp Val Thr Pro Asn Ser Trp
        25                  30                  35

Pro Glu Trp Pro Val Lys Leu Gly Tyr Ile Thr Pro Arg Gly Glu His
40                  45                  50                  55

Leu Ile Ser Leu Met Gly Gly Phe Tyr Arg Gln Lys Phe Gln Gln Lys
                60                  65                  70

Gly Ile Leu Ser Gln Gly Ser Cys Pro Thr Pro Asn Ser Ile Tyr Val
            75                  80                  85

Trp Ala Asp Val Asp Gln Arg Thr Leu Lys Thr Gly Glu Ala Phe Leu
        90                  95                  100

Ala Gly Leu Ala Pro Gln Cys Gly Leu Thr Ile His His Gln Gln Asn
105                 110                 115

Leu Glu Lys Ala Asp Pro Leu Phe His Pro Val Lys Ala Gly Thr Cys
120                 125                 130                 135

Ser Met Asp Lys Thr Gln Val Gln Gln Ala Val Lys Glu Ala Gln
        140                 145                 150

Met Pro Ile Glu Asn Leu Asn Gln His Tyr Ile Pro Ser Leu Ala Leu
            155                 160                 165

Met Asn Thr Thr Leu Asn Phe Ser Thr Ser Ala Trp Cys Gln Lys His
        170                 175                 180

Ser Ala Asp Lys Ser Cys Asp Leu Ala Gln Ser Met Pro Ser Lys Leu
        185                 190                 195

Ser Ile Lys Asp Asn Gly Asn Lys Val Ala Leu Asp Gly Ala Ile Gly
200                 205                 210                 215

Leu Ser Ser Thr Leu Ala Glu Ile Phe Leu Leu Glu Tyr Ala Gln Gly
            220                 225                 230

Met Pro Gln Ala Ala Trp Gly Asn Ile His Ser Glu Gln Glu Trp Ala
        235                 240                 245

Ser Leu Leu Lys Leu His Asn Thr Gln Phe Asp Leu Met Ala Arg Thr
        250                 255                 260

Pro Tyr Ile Ala Ala His Asn Gly Thr Pro Leu Leu Gln Thr Ile Ser
        265                 270                 275

Asn Ala Leu Glu Pro Lys Ala Asp Val Ser Lys Leu Pro Asp Ile Ser
280                 285                 290                 295

Ser Asp Asn Lys Ile Leu Phe Ile Ala Gly His Asp Thr Asn Ile Ala
            300                 305                 310

Asn Ile Ala Gly Met Leu Asn Met Arg Trp Thr Leu Pro Gly Gln Pro
            315                 320                 325

Asp Asn Thr Pro Pro Gly Gly Ala Leu Val Phe Glu Arg Leu Ala Asp
        330                 335                 340

Lys Ser Gly Lys Gln Tyr Ile Ser Val Ser Met Val Tyr Gln Thr Leu
        345                 350                 355

Glu Gln Leu Arg Ala Gln Thr Pro Leu Ser Leu Asn Glu Pro Ala Gly
360                 365                 370                 375

Ser Val Gln Leu Lys Ile Pro Gly Cys Asn Asp Gln Thr Ala Glu Gly
            380                 385                 390

Tyr Cys Pro Leu Ser Thr Phe Thr Arg Val Val Ser Gln Ser Val Glu
        395                 400                 405

Pro Gly Cys Gln Leu Pro
        410

<210> SEQ ID NO 5
<211> LENGTH: 1341
<212> TYPE: DNA
<213> ORGANISM: Buttiauxells agrestis DSM18932
<220> FEATURE:
<221> NAME/KEY: CDS
<222> LOCATION: (1)..(1338)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1338)

<400> SEQUENCE: 5 atg acg ttc tct gcg ttt aac cgc aaa aaa ctg acg ctt cac cct ggt         48
Met Thr Phe Ser Ala Phe Asn Arg Lys Lys Leu Thr Leu His Pro Gly
            -30                 -25                 -20 ctg ttc gta gca ctg agc gcc ata ttt tca tta ggc tct acg gcc tat         96
Leu Phe Val Ala Leu Ser Ala Ile Phe Ser Leu Gly Ser Thr Ala Tyr
        -15                 -10                 -5

```
gcc aac gac act ccc gct tca ggc tac cag gtt gaa aaa gtg gta atc      144
Ala Asn Asp Thr Pro Ala Ser Gly Tyr Gln Val Glu Lys Val Val Ile
 -1   1           5                  10                  15 ctc agc cgc cac ggg gtg cga gca ccc acc aaa atg aca cag acc atg      192
Leu Ser Arg His Gly Val Arg Ala Pro Thr Lys Met Thr Gln Thr Met
                 20                  25                  30 cgc gac gta aca ccc aat acc tgg ccc gaa tgg cca gta aaa ttg ggt      240
Arg Asp Val Thr Pro Asn Thr Trp Pro Glu Trp Pro Val Lys Leu Gly
             35                  40                  45 tat atc acg cca cgc ggt gag cat ctg att agc ctg atg ggc ggg ttt      288
Tyr Ile Thr Pro Arg Gly Glu His Leu Ile Ser Leu Met Gly Gly Phe
         50                  55                  60 tat cgc gag aag ttt caa caa cag ggc att tta tcg cag ggc agt tgc      336
Tyr Arg Glu Lys Phe Gln Gln Gln Gly Ile Leu Ser Gln Gly Ser Cys
     65                  70                  75 ccc gca cca aac tca att tat gtc tgg gca gac gtt gat cag cgc acg      384
Pro Ala Pro Asn Ser Ile Tyr Val Trp Ala Asp Val Asp Gln Arg Thr
 80                  85                  90                  95 ctt aaa act ggc gaa gct ttc ctg gca ggg ctt gct ccg caa tgt ggt      432
Leu Lys Thr Gly Glu Ala Phe Leu Ala Gly Leu Ala Pro Gln Cys Gly
                 100                 105                 110 tta act att cac cac cag cag aat ctt gaa aaa gcc gat ccg ctg ttc      480
Leu Thr Ile His His Gln Gln Asn Leu Glu Lys Ala Asp Pro Leu Phe
             115                 120                 125 cat ccg gtg aaa gcg ggc acg tgt tca atg gat aaa act cag gtc caa      528
His Pro Val Lys Ala Gly Thr Cys Ser Met Asp Lys Thr Gln Val Gln
         130                 135                 140 cag gcc gtt gaa aaa gaa gct caa acc ccc att gat aat ctg aat cag      576
Gln Ala Val Glu Lys Glu Ala Gln Thr Pro Ile Asp Asn Leu Asn Gln
 145                 150                 155 cac tat att ccc tct ctg gcc ttg atg aac acg acc ctc aac ttt tcg      624
His Tyr Ile Pro Ser Leu Ala Leu Met Asn Thr Thr Leu Asn Phe Ser
                 160                 165                 170                 175 acg tct gcc tgg tgt cag aaa cac agc gcg gat aaa agc tgt gat tta      672
Thr Ser Ala Trp Cys Gln Lys His Ser Ala Asp Lys Ser Cys Asp Leu
             180                 185                 190 gcg caa tcc atg ccg agc aag ctg tcg ata aaa gat aat ggc aac aaa      720
Ala Gln Ser Met Pro Ser Lys Leu Ser Ile Lys Asp Asn Gly Asn Lys
         195                 200                 205 gtc gct ctc gac ggg gcc att ggc ctt tcg tct acg ctt gct gaa att      768
Val Ala Leu Asp Gly Ala Ile Gly Leu Ser Ser Thr Leu Ala Glu Ile
     210                 215                 220 ttc ctg ctg gaa tat gcg caa ggg atg ccg caa gcg gcg tgg gga aat      816
Phe Leu Leu Glu Tyr Ala Gln Gly Met Pro Gln Ala Ala Trp Gly Asn
 225                 230                 235 att cat tca gag caa gag tgg gcg tcg cta ctg aaa ctg cat aac gcc      864
Ile His Ser Glu Gln Glu Trp Ala Ser Leu Leu Lys Leu His Asn Ala
 240                 245                 250                 255 cag ttt gat ttg atg gcg cgc aca cct tac atc gcc aca cat aac ggc      912
Gln Phe Asp Leu Met Ala Arg Thr Pro Tyr Ile Ala Thr His Asn Gly
                 260                 265                 270 acg cct tta ttg cag acc atc agc aac gcg ctg gag ccg aaa gcc gac      960
Thr Pro Leu Leu Gln Thr Ile Ser Asn Ala Leu Glu Pro Lys Ala Asp
             275                 280                 285 gta agc aaa ctg cct ggt atc tca cct gac aat aag atc ctg ttt ctt     1008
Val Ser Lys Leu Pro Gly Ile Ser Pro Asp Asn Lys Ile Leu Phe Leu
         290                 295                 300 gcc ggg cac gat acc aat att gcc aat atc gca ggc atg ctc aac atg     1056
Ala Gly His Asp Thr Asn Ile Ala Asn Ile Ala Gly Met Leu Asn Met
 305                 310                 315
```

```
cgc tgg acg cta cca ggg caa ccc gat aac acc cct ccg ggc ggc gct    1104
Arg Trp Thr Leu Pro Gly Gln Pro Asp Asn Thr Pro Pro Gly Gly Ala
320             325                 330                 335 tta gtc ttt gag cgt ttg gcc gat aag tca ggg aaa caa tat gtt agc    1152
Leu Val Phe Glu Arg Leu Ala Asp Lys Ser Gly Lys Gln Tyr Val Ser
            340                 345                 350 gtg agc atg gtg tat cag act ctc gag cag ttg cga tcc caa aca cca    1200
Val Ser Met Val Tyr Gln Thr Leu Glu Gln Leu Arg Ser Gln Thr Pro
                355                 360                 365 ctt agc ctt aat caa cct gcg gga agc gtt cag cta aaa att cct ggc    1248
Leu Ser Leu Asn Gln Pro Ala Gly Ser Val Gln Leu Lys Ile Pro Gly
        370                 375                 380 tgt aac gac cag acg gct gaa gga tac tgc cca ctg tcg aca ttc aca    1296
Cys Asn Asp Gln Thr Ala Glu Gly Tyr Cys Pro Leu Ser Thr Phe Thr
    385                 390                 395 cgc gtg gtt agc caa agc gtg gaa ccc ggc tgc cag cta cag taa        1341
Arg Val Val Ser Gln Ser Val Glu Pro Gly Cys Gln Leu Gln
400                 405                 410
```

<210> SEQ ID NO 6
<211> LENGTH: 446
<212> TYPE: PRT
<213> ORGANISM: Buttiauxells agrestis DSM18932

<400> SEQUENCE: 6

```
Met Thr Phe Ser Ala Phe Asn Arg Lys Lys Leu Thr Leu His Pro Gly
            -30                 -25                 -20

Leu Phe Val Ala Leu Ser Ala Ile Phe Ser Leu Gly Ser Thr Ala Tyr
        -15                 -10                 -5

Ala Asn Asp Thr Pro Ala Ser Gly Tyr Gln Val Glu Lys Val Val Ile
-1  1               5                   10                  15

Leu Ser Arg His Gly Val Arg Ala Pro Thr Lys Met Thr Gln Thr Met
                20                  25                  30

Arg Asp Val Thr Pro Asn Thr Trp Pro Glu Trp Pro Val Lys Leu Gly
            35                  40                  45

Tyr Ile Thr Pro Arg Gly Glu His Leu Ile Ser Leu Met Gly Gly Phe
        50                  55                  60

Tyr Arg Glu Lys Phe Gln Gln Gln Gly Ile Leu Ser Gln Gly Ser Cys
65                  70                  75

Pro Ala Pro Asn Ser Ile Tyr Val Trp Ala Asp Val Asp Gln Arg Thr
80                  85                  90                  95

Leu Lys Thr Gly Glu Ala Phe Leu Ala Gly Leu Ala Pro Gln Cys Gly
                100                 105                 110

Leu Thr Ile His His Gln Gln Asn Leu Glu Lys Ala Asp Pro Leu Phe
            115                 120                 125

His Pro Val Lys Ala Gly Thr Cys Ser Met Asp Lys Thr Gln Val Gln
        130                 135                 140

Gln Ala Val Glu Lys Glu Ala Gln Thr Pro Ile Asp Asn Leu Asn Gln
    145                 150                 155

His Tyr Ile Pro Ser Leu Ala Leu Met Asn Thr Thr Leu Asn Phe Ser
160                 165                 170                 175

Thr Ser Ala Trp Cys Gln Lys His Ser Ala Asp Lys Ser Cys Asp Leu
                180                 185                 190

Ala Gln Ser Met Pro Ser Lys Leu Ser Ile Lys Asp Asn Gly Asn Lys
            195                 200                 205

Val Ala Leu Asp Gly Ala Ile Gly Leu Ser Ser Thr Leu Ala Glu Ile
```

-continued

```
                210                 215                 220
Phe Leu Leu Glu Tyr Ala Gln Gly Met Pro Gln Ala Ala Trp Gly Asn
225                 230                 235

Ile His Ser Glu Gln Glu Trp Ala Ser Leu Leu Lys Leu His Asn Ala
240                 245                 250                 255

Gln Phe Asp Leu Met Ala Arg Thr Pro Tyr Ile Ala Thr His Asn Gly
                260                 265                 270

Thr Pro Leu Leu Gln Thr Ile Ser Asn Ala Leu Glu Pro Lys Ala Asp
                275                 280                 285

Val Ser Lys Leu Pro Gly Ile Ser Pro Asp Asn Lys Ile Leu Phe Leu
                290                 295                 300

Ala Gly His Asp Thr Asn Ile Ala Asn Ile Ala Gly Met Leu Asn Met
                305                 310                 315

Arg Trp Thr Leu Pro Gly Gln Pro Asp Asn Thr Pro Pro Gly Gly Ala
320                 325                 330                 335

Leu Val Phe Glu Arg Leu Ala Asp Lys Ser Gly Lys Gln Tyr Val Ser
                340                 345                 350

Val Ser Met Val Tyr Gln Thr Leu Glu Gln Leu Arg Ser Gln Thr Pro
                355                 360                 365

Leu Ser Leu Asn Gln Pro Ala Gly Ser Val Gln Leu Lys Ile Pro Gly
                370                 375                 380

Cys Asn Asp Gln Thr Ala Glu Gly Tyr Cys Pro Leu Ser Thr Phe Thr
385                 390                 395

Arg Val Val Ser Gln Ser Val Glu Pro Gly Cys Gln Leu Gln
400                 405                 410
```

<210> SEQ ID NO 7
<211> LENGTH: 446
<212> TYPE: PRT
<213> ORGANISM: Artificial Sequence
<220> FEATURE:
<223> OTHER INFORMATION: Synthetic Construct

<400> SEQUENCE: 7

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
                35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Asp Gln Arg Thr
                115                 120                 125

Leu Lys Thr Gly Glu Ala Phe Leu Ala Gly Leu Ala Pro Glu Cys His
                130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
```

```
                165                 170                 175
Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 8
<211> LENGTH: 446
<212> TYPE: PRT
<213> ORGANISM: Artificial sequence
<220> FEATURE:
<223> OTHER INFORMATION: Synthetic construct

<400> SEQUENCE: 8

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Glu Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
```

```
                    85                  90                  95
Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
            130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
            195                 200                 205

Thr Ser Ala Trp Cys Gln Lys His Ser Ala Asp Lys Ser Cys Asp Leu
            210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
            275                 280                 285

Gln Phe Asp Leu Met Ala Arg Thr Pro Tyr Ile Ala Arg His Asn Gly
            290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 9
<211> LENGTH: 446
<212> TYPE: PRT
<213> ORGANISM: Artificial sequence
<220> FEATURE:
<223> OTHER INFORMATION: Snythetic construct

<400> SEQUENCE: 9

Met Thr Ile Ser Ala Phe Asn Arg Lys Lys Leu Thr Leu His Pro Gly
```

-continued

```
1               5                   10                  15
Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
 50                  55                  60

Arg Asp Val Thr Pro Asn Thr Trp Pro Glu Trp Pro Val Lys Leu Gly
 65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
            130                 135                 140

Leu Thr Ile His His Gln Gln Asp Ile Lys Lys Ala Asp Pro Leu Phe
145                 150                 155                 160

His Pro Val Lys Ala Gly Val Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
                195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
            290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430
```

Arg Val Val Ser Gln Ser Val Glu Pro Gly Cys Gln Leu Gln
            435                 440                 445

<210> SEQ ID NO 10
<211> LENGTH: 446
<212> TYPE: PRT
<213> ORGANISM: Artificial sequence
<220> FEATURE:
<223> OTHER INFORMATION: Synthetic construct

<400> SEQUENCE: 10

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Thr
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
        370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 11
<211> LENGTH: 446
<212> TYPE: PRT
<213> ORGANISM: Artificial sequence
<220> FEATURE:
<223> OTHER INFORMATION: Synthetic construct

<400> SEQUENCE: 11

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
        435                 440                 445

<210> SEQ ID NO 12
<211> LENGTH: 446
<212> TYPE: PRT
<213> ORGANISM: Artificial sequence
<220> FEATURE:
<223> OTHER INFORMATION: Synthetic construct

<400> SEQUENCE: 12

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
    130                 135                 140

Leu Thr Ile His His Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
            195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 13
<211> LENGTH: 446
<212> TYPE: PRT
<213> ORGANISM: Artificial sequence
<220> FEATURE:
<223> OTHER INFORMATION: Synthetic construct

<400> SEQUENCE: 13

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Lys
225                 230                 235                 240

Val Ala Leu Cys Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 14
<211> LENGTH: 446
<212> TYPE: PRT
<213> ORGANISM: Artificial sequence
<220> FEATURE:
<223> OTHER INFORMATION: Synthetic construct

<400> SEQUENCE: 14

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

-continued

```
Ala Asn Asp Thr Pro Ala Ser Gly Tyr Gln Val Glu Lys Val Val Ile
         35                  40                  45
Leu Ser Arg His Gly Val Arg Ala Pro Thr Lys Met Thr Gln Thr Met
 50                  55                  60
Arg Asp Val Thr Pro Asn Thr Trp Pro Glu Trp Pro Val Lys Leu Gly
 65                  70                  75                  80
Tyr Ile Thr Pro Arg Gly Glu His Leu Ile Ser Leu Met Gly Gly Phe
                 85                  90                  95
Tyr Arg Gln Lys Phe Gln Gln Gly Ile Leu Ser Gln Gly Ser Cys
                100                 105                 110
Pro Thr Pro Asn Ser Ile Tyr Val Trp Ala Asp Val Asp Gln Arg Thr
                115                 120                 125
Leu Lys Thr Gly Glu Ala Phe Leu Ala Gly Leu Ala Pro Glu Cys His
            130                 135                 140
Leu Thr Ile His His Gln Gln Asp Ile Lys Lys Ala Asp Pro Leu Phe
145                 150                 155                 160
His Pro Val Lys Ala Gly Thr Cys Ser Met Asp Lys Thr Gln Val Gln
                165                 170                 175
Gln Ala Val Glu Lys Glu Ala Gln Thr Pro Ile Asp Asn Leu Asn Gln
            180                 185                 190
His Tyr Ile Pro Phe Leu Ala Leu Met Asn Thr Thr Leu Asn Phe Ser
                195                 200                 205
Thr Ser Ala Trp Cys Gln Lys His Ser Ala Asp Lys Ser Cys Asp Leu
        210                 215                 220
Gly Leu Ser Met Pro Ser Lys Leu Ser Ile Lys Asp Asn Gly Asn Lys
225                 230                 235                 240
Val Ala Leu Asp Gly Ala Ile Gly Leu Ser Ser Thr Leu Ala Glu Ile
                245                 250                 255
Phe Leu Leu Glu Tyr Ala Gln Gly Met Pro Gln Ala Ala Trp Gly Asn
            260                 265                 270
Ile His Ser Glu Gln Glu Trp Ala Ser Leu Leu Lys Leu His Asn Val
        275                 280                 285
Tyr Phe Asp Leu Met Ala Arg Thr Pro Tyr Ile Ala Arg His Asn Gly
        290                 295                 300
Thr Pro Leu Leu Gln Ala Ile Ser Asn Ala Leu Asn Pro Asn Ala Thr
305                 310                 315                 320
Glu Ser Lys Leu Pro Asp Ile Ser Pro Asp Asn Lys Ile Leu Phe Ile
                325                 330                 335
Ala Gly His Asp Thr Asn Ile Ala Asn Ile Ala Gly Met Leu Asn Met
            340                 345                 350
Arg Trp Thr Leu Pro Gly Gln Pro Asp Asn Thr Pro Pro Gly Gly Ala
        355                 360                 365
Leu Val Phe Glu Arg Leu Ala Asp Lys Ser Gly Lys Gln Tyr Val Ser
        370                 375                 380
Val Ser Met Val Tyr Gln Thr Leu Glu Gln Leu Arg Ser Gln Thr Pro
385                 390                 395                 400
Leu Ser Leu Asn Gln Pro Ala Gly Ser Val Gln Leu Lys Ile Pro Gly
                405                 410                 415
Cys Asn Asp Gln Thr Ala Glu Gly Tyr Cys Pro Leu Ser Thr Phe Thr
            420                 425                 430
Arg Val Val Ser Gln Ser Val Glu Pro Gly Cys Gln Leu Gln
        435                 440                 445
```

<210> SEQ ID NO 15
<211> LENGTH: 446
<212> TYPE: PRT
<213> ORGANISM: Artificial sequence
<220> FEATURE:
<223> OTHER INFORMATION: Synthetic construct

<400> SEQUENCE: 15

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Lys Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365
```

```
Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 16
<211> LENGTH: 446
<212> TYPE: PRT
<213> ORGANISM: Artificial sequence
<220> FEATURE:
<223> OTHER INFORMATION: Synthetic construct

<400> SEQUENCE: 16

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
            130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Ser Leu Ala Leu Met Asn Thr Thr Leu Asn Phe Ser
            195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
            275                 280                 285
```

```
Gln Phe Asp Leu Met Ala Arg Thr Pro Tyr Ile Ala Arg His Asn Gly
    290                 295                 300
Thr Pro Leu Leu Gln Ala Ile Ser Asn Ala Leu Asn Pro Asn Ala Thr
305                 310                 315                 320
Glu Ser Lys Leu Pro Asp Ile Ser Pro Asp Asn Lys Ile Leu Phe Ile
                325                 330                 335
Ala Gly His Asp Thr Asn Ile Ala Asn Ile Ala Gly Met Leu Asn Met
                340                 345                 350
Arg Trp Thr Leu Pro Gly Gln Pro Asp Asn Thr Pro Pro Gly Gly Ala
                355                 360                 365
Leu Val Phe Glu Arg Leu Ala Asp Lys Ser Gly Lys Gln Tyr Val Ser
    370                 375                 380
Val Ser Met Val Tyr Gln Thr Leu Glu Gln Leu Arg Ser Gln Thr Pro
385                 390                 395                 400
Leu Ser Leu Asn Gln Pro Ala Gly Ser Val Gln Leu Lys Ile Pro Gly
                405                 410                 415
Cys Asn Asp Gln Thr Ala Glu Gly Tyr Cys Pro Leu Ser Thr Phe Thr
                420                 425                 430
Arg Val Val Ser Gln Ser Val Glu Pro Gly Cys Gln Leu Gln
                435                 440                 445
```

<210> SEQ ID NO 17
<211> LENGTH: 446
<212> TYPE: PRT
<213> ORGANISM: Artificial sequence
<220> FEATURE:
<223> OTHER INFORMATION: Synthetic construct

<400> SEQUENCE: 17

```
Met Thr Ile Ser Ala Phe Asn Arg Lys Lys Leu Thr Leu His Pro Gly
1               5                   10                  15
Leu Phe Val Ala Leu Ser Ala Ile Phe Ser Leu Gly Ser Thr Ala Tyr
                20                  25                  30
Ala Asn Asp Thr Pro Ala Ser Gly Tyr Gln Val Glu Lys Val Val Ile
                35                  40                  45
Leu Ser Arg His Gly Val Arg Ala Pro Thr Lys Met Thr Gln Thr Met
    50                  55                  60
Arg Asp Val Thr Pro Asn Thr Trp Pro Glu Trp Pro Val Lys Leu Gly
65                  70                  75                  80
Tyr Ile Thr Pro Arg Gly Glu His Leu Ile Ser Leu Met Gly Gly Phe
                85                  90                  95
Tyr Arg Gln Lys Phe Gln Gln Gly Ile Leu Ser Gln Gly Ser Cys
                100                 105                 110
Pro Thr Pro Asn Ser Ile Tyr Val Trp Ala Asp Val Glu Gln Arg Thr
                115                 120                 125
Leu Lys Thr Gly Glu Ala Phe Leu Ala Gly Leu Ala Pro Glu Cys His
    130                 135                 140
Leu Thr Ile His His Gln Asp Ile Lys Lys Ala Asp Pro Leu Phe
145                 150                 155                 160
His Pro Val Lys Ala Gly Thr Cys Ser Met Asp Lys Thr Gln Val Gln
                165                 170                 175
Gln Ala Val Glu Lys Glu Ala Gln Thr Pro Ile Asp Asn Leu Asn Gln
                180                 185                 190
Arg Tyr Ile Pro Phe Leu Ala Leu Met Asn Thr Thr Leu Asn Phe Ser
                195                 200                 205
```

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
                275                 280                 285

Gln Phe Asp Leu Met Ala Arg Thr Pro Tyr Ile Ala Arg His Asn Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
                435                 440                 445

<210> SEQ ID NO 18
<211> LENGTH: 446
<212> TYPE: PRT
<213> ORGANISM: Artificial sequence
<220> FEATURE:
<223> OTHER INFORMATION: Synthetic construct

<400> SEQUENCE: 18

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
                35                  40                  45

Leu Ser Arg His Gly Val Arg Ala Pro Thr Lys Met Thr Gln Thr Met
                50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Asp Gln Arg Thr
                115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 19
<211> LENGTH: 446
<212> TYPE: PRT
<213> ORGANISM: Artificial sequence
<220> FEATURE:
<223> OTHER INFORMATION: Synthetic construct

<400> SEQUENCE: 19

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

-continued

```
Leu Ser Arg His Gly Val Arg Ala Pro Thr Lys Met Thr Gln Thr Met
 50                  55                  60
Arg Asp Val Thr Pro Asn Thr Trp Pro Glu Trp Pro Val Lys Leu Gly
 65                  70                  75                  80
Tyr Ile Thr Pro Arg Gly Glu His Leu Ile Ser Leu Met Gly Gly Phe
                 85                  90                  95
Tyr Arg Gln Lys Phe Gln Gln Gly Ile Leu Ser Gln Gly Ser Cys
            100                 105                 110
Pro Thr Pro Asn Ser Ile Tyr Val Trp Ala Asp Val Asp Gln Arg Thr
            115                 120                 125
Leu Lys Thr Gly Glu Ala Phe Leu Ala Gly Leu Ala Pro Glu Cys His
130                 135                 140
Leu Thr Ile His His Gln Asp Ile Lys Lys Ala Asp Pro Leu Phe
145                 150                 155                 160
His Pro Val Lys Ala Gly Ile Cys Ser Met Asp Lys Thr Gln Val Gln
                165                 170                 175
Gln Ala Val Glu Lys Glu Ala Gln Thr Pro Ile Asp Asn Leu Asn Gln
            180                 185                 190
His Tyr Ile Pro Phe Leu Ala Leu Met Asn Thr Thr Leu Asn Phe Ser
            195                 200                 205
Thr Ser Ala Trp Cys Gln Lys His Ser Ala Asp Lys Ser Cys Asp Leu
210                 215                 220
Gly Leu Ser Met Pro Ser Lys Leu Ser Ile Lys Asp Asn Gly Asn Thr
225                 230                 235                 240
Val Ala Leu Asp Gly Ala Ile Gly Leu Ser Ser Thr Leu Ala Glu Ile
                245                 250                 255
Phe Leu Leu Glu Tyr Ala Gln Gly Met Pro Gln Ala Ala Trp Gly Asn
            260                 265                 270
Ile His Ser Glu Gln Glu Trp Ala Ser Leu Leu Lys Leu His Asn Val
            275                 280                 285
Gln Phe Asp Leu Met Ala Arg Thr Pro Tyr Ile Ala Arg His Asn Gly
290                 295                 300
Thr Pro Leu Leu Gln Ala Ile Ser Asn Ala Leu Asn Pro Asn Ala Thr
305                 310                 315                 320
Glu Ser Lys Leu Pro Asp Ile Ser Pro Asp Asn Lys Ile Leu Phe Ile
                325                 330                 335
Ala Gly His Asp Thr Asn Ile Ala Asn Ile Ala Gly Met Leu Asn Met
            340                 345                 350
Arg Trp Thr Leu Pro Gly Gln Pro Asp Asn Thr Pro Pro Gly Gly Ala
            355                 360                 365
Leu Val Phe Glu Arg Leu Ala Asp Lys Ser Gly Lys Gln Tyr Val Ser
370                 375                 380
Val Ser Met Val Tyr Gln Thr Leu Glu Gln Leu Arg Ser Gln Thr Pro
385                 390                 395                 400
Leu Ser Leu Asn Gln Pro Ala Gly Ser Val Gln Leu Lys Ile Pro Gly
                405                 410                 415
Cys Asn Asp Gln Thr Ala Glu Gly Tyr Cys Pro Leu Ser Thr Phe Thr
            420                 425                 430
Arg Val Val Ser Gln Ser Val Glu Pro Gly Cys Gln Leu Gln
            435                 440                 445

<210> SEQ ID NO 20
<211> LENGTH: 446
<212> TYPE: PRT
```

<213> ORGANISM: Artificial sequence
<220> FEATURE:
<223> OTHER INFORMATION: Synthetic construct

<400> SEQUENCE: 20

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
                100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Glu Leu
210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asp Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
```

```
                385                 390                 395                 400
Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
                435                 440                 445
```

<210> SEQ ID NO 21
<211> LENGTH: 446
<212> TYPE: PRT
<213> ORGANISM: Artificial sequence
<220> FEATURE:
<223> OTHER INFORMATION: Synthetic construct

<400> SEQUENCE: 21

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
                35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Asp Gln Arg Thr
                115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
                180                 185                 190

His Tyr Ile Pro Phe Leu Ala Leu Met Asn Thr Thr Leu Asn Phe Ser
                195                 200                 205

Thr Ser Ala Trp Cys Gln Lys His Ser Ala Asp Lys Ser Cys Asp Leu
        210                 215                 220

Gly Leu Ser Met Pro Ser Lys Leu Ser Ile Lys Asp Asn Gly Asn Thr
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
                275                 280                 285

Gln Phe Asp Leu Met Glu Arg Thr Pro Tyr Ile Ala Arg His Lys Gly
        290                 295                 300

Thr Pro Leu Leu Gln Ala Ile Ser Asn Ala Leu Asn Pro Asn Ala Thr
```

```
305                 310                 315                 320
Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
                355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
                435                 440                 445

<210> SEQ ID NO 22
<211> LENGTH: 446
<212> TYPE: PRT
<213> ORGANISM: Artificial sequence
<220> FEATURE:
<223> OTHER INFORMATION: Synthetic construct

<400> SEQUENCE: 22

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Glu
```

```
                225                 230                 235                 240

Val Ser Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
                275                 280                 285

Gln Phe Asp Leu Met Glu Arg Thr Pro Tyr Ile Ala Arg His Lys Gly
            290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
                355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
            435                 440                 445

<210> SEQ ID NO 23
<211> LENGTH: 446
<212> TYPE: PRT
<213> ORGANISM: Artificial sequence
<220> FEATURE:
<223> OTHER INFORMATION: Synthetic construct

<400> SEQUENCE: 23

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Thr Asp Val Asp Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
```

```
            145                 150                 155                 160
His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Ser Leu Ala Leu Met Asn Thr Thr Leu Asn Phe Ser
        195                 200                 205

Lys Ser Pro Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 24
<211> LENGTH: 446
<212> TYPE: PRT
<213> ORGANISM: Artificial sequence
<220> FEATURE:
<223> OTHER INFORMATION: Synthetic construct

<400> SEQUENCE: 24

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
```

```
                65                  70                  75                  80
        Tyr Ile Thr Pro Arg Gly Glu His Leu Ile Ser Leu Met Gly Gly Phe
                            85                  90                  95

Tyr Arg Gln Lys Phe Gln Gln Gly Ile Leu Ser Gln Gly Ser Cys
                        100                 105                 110

Pro Thr Pro Asn Ser Ile Tyr Val Trp Thr Asp Val Asp Gln Arg Thr
                        115                 120                 125

Leu Lys Thr Gly Glu Ala Phe Leu Ala Gly Leu Ala Pro Glu Cys His
                    130                 135                 140

Leu Thr Ile His His Gln Gln Asp Ile Lys Lys Ala Asp Pro Leu Phe
        145                 150                 155                 160

His Pro Val Lys Ala Gly Ile Cys Ser Met Asp Lys Thr Gln Val Gln
                            165                 170                 175

Gln Ala Val Glu Lys Glu Ala Gln Thr Pro Ile Asp Asn Leu Asn Gln
                        180                 185                 190

His Tyr Ile Pro Ser Leu Ala Leu Met Asn Thr Thr Leu Asn Phe Ser
                        195                 200                 205

Lys Ser Pro Trp Cys Gln Lys His Ser Ala Asp Lys Ser Cys Asp Leu
                    210                 215                 220

Gly Leu Ser Met Pro Ser Lys Leu Ser Ile Lys Asp Asn Gly Asn Glu
        225                 230                 235                 240

Val Ser Leu Asp Gly Ala Ile Gly Leu Ser Ser Thr Leu Ala Glu Ile
                            245                 250                 255

Phe Leu Leu Glu Tyr Ala Gln Gly Met Pro Gln Ala Ala Trp Gly Asn
                        260                 265                 270

Ile His Ser Glu Gln Glu Trp Ala Leu Leu Lys Leu His Asn Val
                    275                 280                 285

Tyr Phe Asp Leu Met Glu Arg Thr Pro Tyr Ile Ala Arg His Lys Gly
                    290                 295                 300

Thr Pro Leu Leu Gln Ala Ile Ser Asn Ala Leu Asn Pro Asn Ala Thr
        305                 310                 315                 320

Glu Ser Lys Leu Pro Asp Ile Ser Pro Asp Asn Lys Ile Leu Phe Ile
                        325                 330                 335

Ala Gly His Asp Thr Asn Ile Ala Asn Ile Ala Gly Met Leu Asn Met
                    340                 345                 350

Arg Trp Thr Leu Pro Gly Gln Pro Asp Asn Thr Pro Gly Gly Ala
                    355                 360                 365

Leu Val Phe Glu Arg Leu Ala Asp Lys Ser Gly Lys Gln Tyr Val Ser
                    370                 375                 380

Val Ser Met Val Tyr Gln Thr Leu Glu Gln Leu Arg Ser Gln Thr Pro
        385                 390                 395                 400

Leu Ser Leu Asn Gln Pro Ala Gly Ser Val Gln Leu Lys Ile Pro Gly
                        405                 410                 415

Cys Asn Asp Gln Thr Ala Glu Gly Tyr Cys Pro Leu Ser Thr Phe Thr
                        420                 425                 430

Arg Val Val Ser Gln Ser Val Glu Pro Gly Cys Gln Leu Gln
                    435                 440                 445

<210> SEQ ID NO 25
<211> LENGTH: 446
<212> TYPE: PRT
<213> ORGANISM: Artificial sequence
<220> FEATURE:
<223> OTHER INFORMATION: Synthetic construct
```

<400> SEQUENCE: 25

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gly Ser Cys
            100                 105                 110

Pro Thr Pro Asn Ser Ile Tyr Val Trp Thr Asp Val Glu Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

Arg Tyr Ile Pro Ser Leu Ala Leu Met Asn Thr Thr Leu Asn Phe Ser
        195                 200                 205

Lys Ser Pro Trp Cys Gln Lys His Ser Ala Asp Lys Asn Cys Asp Leu
210                 215                 220

Ala Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415
```

```
Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 26
<211> LENGTH: 446
<212> TYPE: PRT
<213> ORGANISM: Artificial sequence
<220> FEATURE:
<223> OTHER INFORMATION: Synthetic construct

<400> SEQUENCE: 26

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
                35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Glu Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

Arg Tyr Ile Pro Ser Leu Ala Leu Met Asn Thr Ile Leu Asn Phe Ser
        195                 200                 205

Lys Ser Pro Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Val Ala Trp Gly Asn
            260                 265                 270

Ile His Ser Glu Gln Glu Trp Ala Ser Leu Leu Lys Leu His Asn Val
        275                 280                 285

His Phe Asp Leu Met Glu Arg Thr Pro Tyr Ile Ala Arg His Lys Gly
        290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335
```

```
Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
            435                 440                 445

<210> SEQ ID NO 27
<211> LENGTH: 446
<212> TYPE: PRT
<213> ORGANISM: Artificial sequence
<220> FEATURE:
<223> OTHER INFORMATION: Synthetic construct

<400> SEQUENCE: 27

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Thr Asp Val Asp Gln Arg Thr
            115                 120                 125

Leu Lys Thr Gly Glu Ala Phe Leu Ala Gly Leu Ala Pro Glu Cys His
            130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

Arg Tyr Ile Pro Ser Leu Ala Leu Met Asn Thr Ile Leu Asn Phe Ser
            195                 200                 205

Lys Ser Pro Trp Cys Gln Lys His Ser Ala Asp Lys Ser Cys Asp Leu
            210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255
```

```
Phe Leu Leu Glu Tyr Ala Gln Gly Met Pro Gln Val Ala Trp Gly Asn
            260                 265                 270

Ile His Ser Glu Gln Glu Trp Ala Ser Leu Leu Lys Leu His Asn Val
        275                 280                 285

His Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Phe
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445
```

```
<210> SEQ ID NO 28
<211> LENGTH: 446
<212> TYPE: PRT
<213> ORGANISM: Artificial sequence
<220> FEATURE:
<223> OTHER INFORMATION: Synthetic construct

<400> SEQUENCE: 28

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
    50                  55                  60

Arg Asp Val Thr Pro Tyr Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Glu Gln Arg Thr
            115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175
```

```
Gln Ala Val Glu Lys Glu Ala Gln Thr Pro Ile Asp Asn Leu Asn Gln
            180                 185                 190

Arg Tyr Ile Pro Ser Leu Ala Leu Met Asn Thr Ile Leu Asn Phe Ser
            195                 200                 205

Lys Ser Pro Trp Cys Gln Lys His Ser Ala Asp Lys Ser Cys Asp Leu
            210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
            245                 250                 255

Phe Leu Leu Glu Tyr Ala Gln Gly Met Pro Gln Val Ala Trp Gly Asn
            260                 265                 270

Ile His Ser Glu Gln Glu Trp Ala Ser Leu Leu Lys Leu His Asn Val
            275                 280                 285

His Phe Asp Leu Met Glu Arg Thr Pro Tyr Ile Ala Arg His Lys Gly
            290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
            325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 29
<211> LENGTH: 444
<212> TYPE: PRT
<213> ORGANISM: Obesumbacterium proteus

<400> SEQUENCE: 29

Met Thr Ile Ser Leu Phe Thr His Ser Pro Thr Arg Leu Leu Lys Cys
1               5                   10                  15

Met Pro Leu Ala Phe Ile Ala Ala Ser Met Leu Thr Thr Ala Ser Tyr
            20                  25                  30

Ala Ser Glu Thr Glu Pro Ser Gly Tyr Gln Leu Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Ala Trp Pro Glu Trp Pro Val Lys Leu Gly
65                  70                  75                  80

Tyr Ile Thr Pro Arg Gly Glu His Leu Val Ser Leu Met Gly Gly Phe
            85                  90                  95

Tyr Arg Gln Lys Phe Gln Gln Leu Gly Ile Leu Ser Lys Gly Arg Cys
            100                 105                 110
```

```
Pro Thr Ala Asn Asp Val Tyr Val Trp Ala Asp Val Asp Gln Arg Thr
            115                 120                 125
Arg Lys Thr Gly Glu Ala Phe Leu Ala Gly Leu Ala Pro Glu Cys His
        130                 135                 140
Leu Ser Ile His His Gln Gln Asp Ile Lys Gln Ala Asp Pro Leu Phe
145                     150                 155                 160
His Pro Val Lys Ala Gly Val Cys Thr Met Glu Lys Thr Gln Val Gln
                165                 170                 175
Gln Ala Val Glu Gln Gln Ala Gly Met Pro Ile Asp Gln Leu Asn Gln
            180                 185                 190
His Tyr Arg Pro Ala Leu Ala Leu Met Ser Ser Val Leu Asn Phe Pro
        195                 200                 205
Lys Ser Thr Tyr Cys Gln Gln His Ser Ala Asp Gln Thr Cys Asp Leu
        210                 215                 220
Ala Gln Ala Met Pro Ser Lys Leu Ser Ile Lys Asp Asn Gly Asn Lys
225                 230                 235                 240
Val Ala Leu Asp Gly Ala Val Gly Leu Ser Ser Thr Leu Ala Glu Ile
                245                 250                 255
Phe Leu Leu Glu Tyr Ala Gln Gly Met Pro Asp Ala Ala Trp Gly Lys
                260                 265                 270
Ile His Ser Glu Gln Asp Trp Asn Ala Leu Leu Thr Leu His Asn Ala
        275                 280                 285
Gln Phe Asp Leu Met Ser Arg Thr Pro Tyr Ile Ala Lys His Asn Gly
        290                 295                 300
Thr Pro Leu Leu Gln Thr Ile Val Ser Ala Ile Asn Ser Gln Pro Ser
305                 310                 315                 320
Ser Arg Glu Leu Pro Glu Leu Ser Ala Asp Asn Lys Ile Leu Phe Pro
                325                 330                 335
Ala Gly His Asp Thr Asn Ile Ala Asn Ile Ala Gly Met Phe Gly Met
            340                 345                 350
Ser Trp Ala Leu Pro Gly Gln Pro Asp Asn Thr Pro Pro Gly Gly Ala
        355                 360                 365
Leu Val Phe Glu Arg Trp Ser Asp Lys Thr Gly Lys Lys Tyr Val Ser
        370                 375                 380
Val Gln Met Met Tyr Gln Thr Leu Ala Gln Leu Arg Asn Gln Thr Pro
385                 390                 395                 400
Leu Thr Leu Asp Lys Pro Ala Gly Ser Val Ala Leu Lys Ile Pro Gly
                405                 410                 415
Cys Asp Asp Gln Thr Ala Glu Gly Tyr Cys Pro Leu Asp Thr Phe Thr
            420                 425                 430
Arg Leu Ala Lys Gln Asn Glu Leu Val Glu Cys Gln
        435                 440
```